(12) United States Patent
Bowling

(10) Patent No.: US 11,253,329 B2
(45) Date of Patent: Feb. 22, 2022

(54) ROBOTIC SURGICAL SYSTEM AND METHOD FOR PRODUCING REACTIVE FORCES TO IMPLEMENT VIRTUAL BOUNDARIES

(71) Applicant: MAKO Surgical Corp., Ft. Lauderdale, FL (US)

(72) Inventor: David Gene Bowling, Los Ranchos de Albuquerque, NM (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 444 days.

(21) Appl. No.: 16/000,498

(22) Filed: Jun. 5, 2018

(65) Prior Publication Data

US 2018/0353253 A1 Dec. 13, 2018

Related U.S. Application Data

(60) Provisional application No. 62/517,453, filed on Jun. 9, 2017.

(51) Int. Cl.
*A61B 34/30* (2016.01)
*B25J 9/16* (2006.01)
(Continued)

(52) U.S. Cl.
CPC ...... *A61B 34/70* (2016.02); *A61B 17/320068* (2013.01); *A61B 34/10* (2016.02);
(Continued)

(58) Field of Classification Search
CPC ......... A61B 34/32; A61B 34/70; A61B 34/30; A61B 34/76; A61B 34/10; A61B 34/20;
(Continued)

(56) References Cited

U.S. PATENT DOCUMENTS 5,694,013 A * 12/1997 Stewart .................. B25J 9/1656
318/561
5,769,640 A * 6/1998 Jacobus ................. B25J 9/1689
434/262

(Continued)

OTHER PUBLICATIONS

Fisher, S. et al., "Fast Penetration Depth Estimation for Elastic Bodies Using Deformed Distance Fields", Proceedings of the 2001 IEEE/RSJ International Conference on Intelligent Robots and Systems, vol. 1, Oct. 29, 2001, pp. 330-336.

(Continued)

*Primary Examiner* — Stephen Holwerda
(74) *Attorney, Agent, or Firm* — Howard & Howard Attorneys PLLC

(57) ABSTRACT

A robotic system and methods are provided. The robotic system includes a tool and a manipulator with links for moving the tool. A controller implements a virtual simulation wherein the tool is represented as a virtual volume interacting with a virtual boundary defined by a mesh of polygonal elements. The controller computes a reactive force responsive to penetration of polygonal elements by the virtual volume. The reactive force is computed based on a penetration factor being a function of a geometry of the virtual volume bound relative to a geometry of the polygonal element. The controller applies the reactive force to the virtual volume to reduce penetration of the polygonal element by the virtual volume. The controller commands the (Continued)

manipulator to move the tool in accordance with application of the reactive force to the virtual volume to constrain movement of the tool relative to the virtual boundary.

23 Claims, 10 Drawing Sheets

(51) Int. Cl.
*A61B 34/00* (2016.01)
*A61B 34/20* (2016.01)
*A61B 17/32* (2006.01)
*A61B 34/32* (2016.01)
*A61B 34/10* (2016.01)
*A61B 90/11* (2016.01)
*A61B 5/06* (2006.01)
*A61B 17/16* (2006.01)
*A61B 90/00* (2016.01)
*A61B 17/14* (2006.01)

(52) U.S. Cl.
CPC .............. *A61B 34/20* (2016.02); *A61B 34/30* (2016.02); *A61B 34/32* (2016.02); *A61B 34/76* (2016.02); *B25J 9/1633* (2013.01); *A61B 5/064* (2013.01); *A61B 17/14* (2013.01); *A61B 17/16* (2013.01); *A61B 90/11* (2016.02); *A61B 2034/101* (2016.02); *A61B 2034/2051* (2016.02); *A61B 2034/2055* (2016.02); *A61B 2034/2059* (2016.02); *A61B 2034/2063* (2016.02); *A61B 2034/2065* (2016.02); *A61B 2034/2068* (2016.02); *A61B 2034/301* (2016.02); *A61B 2090/066* (2016.02); *A61B 2090/378* (2016.02); *G05B 2219/40122* (2013.01); *G05B 2219/45117* (2013.01)

(58) Field of Classification Search
CPC . A61B 17/320068; A61B 17/16; A61B 17/14; A61B 2090/066; A61B 2034/2051; A61B 2034/2055; A61B 2034/2059; A61B 2034/2063; A61B 2034/2065; A61B 90/11; A61B 5/064; A61B 2034/301; A61B 2034/101; A61B 2034/2068; A61B 2090/378; B25J 9/1633; G05B 2219/40122; G05B 2219/45117
See application file for complete search history.

(56) References Cited

U.S. PATENT DOCUMENTS

| | | | |
|---|---|---|---|
| 6,088,020 A * | 7/2000 | Mor | G06F 3/016 318/628 |
| 6,191,796 B1 | 2/2001 | Tarr | |
| 6,211,848 B1 * | 4/2001 | Plesniak | G06F 3/016 345/156 |
| 6,421,048 B1 * | 7/2002 | Shih | G06F 3/016 345/419 |
| 6,792,398 B1 * | 9/2004 | Handley | G06F 3/016 703/2 |
| 7,084,867 B1 * | 8/2006 | Ho | G06F 3/016 345/419 |
| 8,010,180 B2 | 8/2011 | Quaid et al. | |
| 8,571,628 B2 | 10/2013 | Kang et al. | |
| 9,008,757 B2 | 4/2015 | Wu | |
| 9,119,655 B2 | 9/2015 | Bowling et al. | |
| 9,588,583 B2 | 3/2017 | Lightcap et al. | |
| 2004/0128026 A1 * | 7/2004 | Harris | A61B 34/76 700/245 |
| 2005/0116673 A1 * | 6/2005 | Carl | A61B 17/1626 318/432 |
| 2006/0142657 A1 | 6/2006 | Quaid et al. | |
| 2007/0142751 A1 * | 6/2007 | Kang | A61N 1/0534 600/587 |
| 2012/0030429 A1 | 2/2012 | Synge | |
| 2012/0176306 A1 | 7/2012 | Lightcap et al. | |
| 2014/0276943 A1 | 9/2014 | Bowling et al. | |
| 2014/0276949 A1 | 9/2014 | Staunton et al. | |
| 2018/0168750 A1 | 6/2018 | Staunton et al. | |

OTHER PUBLICATIONS

Garethrees.org, "Triangle Circle Intersections", Feb. 19, 2009, 1 page.
International Search Report for Application No. PCT/US2018/036029 dated Sep. 26, 2018, 4 pages.
Tang, Min et al., "Continuous Penalty Forces", ACM Transactions on Graphics, vol. 31, No. 4, Jul. 1, 2012, pp. 1-9.
Teschner, M. et al., "Collision Detection for Deformable Objects", Computer Graphics Forum, vol. 24, No. 1, Mar. 1, 2005, pp. 61-81.
Volino, Pascal et al., "Resolving Surface Collisions Through Intersection Contour Minimization", ACM Transations on Graphics, vol. 25, No. 3, Jul. 1, 2006, pp. 1154-1159.

* cited by examiner $A_{proj} = A_{sector} + A_{tri}$ $A_{proj} = A_{sector} - A_{tri}$

ROBOTIC SURGICAL SYSTEM AND METHOD FOR PRODUCING REACTIVE FORCES TO IMPLEMENT VIRTUAL BOUNDARIES

CROSS-REFERENCE TO RELATED APPLICATIONS

The subject application claims the benefit of U.S. Provisional Patent Application Ser. No. 62/517,453, filed on Jun. 9, 2017, the disclosure of which is hereby incorporated by reference in its entirety.

TECHNICAL FIELD

The present disclosure relates to techniques for producing reactive forces to implement virtual boundaries for a robotic system.

BACKGROUND

Robotic systems are commonly used to perform surgical procedures and include a robot comprising a robotic arm and a tool coupled to an end of the robotic arm for engaging a surgical site.

To prevent the tool from reaching undesired areas, a virtual surface is often implemented for constraining movement of the tool. For instance, the virtual surface may be registered to the surgical site to delineate areas where the tool should and should not manipulate the anatomy.

The virtual surface is often defined as a mesh of polygonal elements, such as triangles. If a force is applied to the tool in attempt to penetrate the virtual surface, a counter force is computed for each triangle of the mesh that experiences this attempted penetration. In other words, when the tool pushes on the virtual surface, the virtual surface pushes back due to the compression of the virtual surface or the tool. Conventionally, this counter force is modeled as a spring and the magnitude of this counter force is proportional to a linear depth of the penetration of the triangle (i.e., a distance by which the tool protrudes into the virtual surface). In turn, the robotic arm moves the tool according to the computed counter forces to constrain the tool relative to the virtual surface.

Modeling and computing these counter forces is anything but trivial. The virtual surfaces often are complex in shape and define geometric features for which surface interaction by the tool is difficult to model. The issue is exacerbated because of the modeled shape of the tool and/or the pose of the tool during penetration.

In turn, when the tool attempts to penetrate the virtual surface, and in particular, when the tool simultaneously penetrates multiple triangles, it has been observed that the robotic arm may provide inconsistent or unexpected movement of the tool responsive to the computed counter forces. For example, as the tool is moved around a flat virtual surface, the tool conventionally experiences a kick-back, interpreted as two counter forces, when simultaneously engaging more than one triangle. The more planar the virtual surface, the worse the kick-back will be. Worse still is when the tool engages a vertex shared among multiple triangles. For example if the vertex is shared among five triangles, the momentary increase of counter force at the vertex will be five times the counter force of one triangle.

Additionally, as the tool rolls over an outside corner defined by the virtual surface, many triangles of the mesh along the edges of the outside corner simultaneously experience the attempted penetration. The counter forces for these triangles, when combined, provide a cumulative force spike causing unexpected kick back of the tool while rolling over the outside corner.

Further complications arise in conventional robotic systems based on modeling surface interactions simply based on the linear depth of penetration, regardless of whether one or multiple triangles are penetrated. For example, there may be situations where the linear depth of penetration is the same, yet the cross sectional area or displaced volume of the virtual surface is different (e.g., based on the modeled shape of the tool or the pose of the tool during penetration, etc.). In such situations, conventional surface modeling applies the same counter force based simply on the linear depth of penetration without taking into account the cross sectional area or displaced volume of the virtual surface.

Similar situations arise where only a portion of the tool penetrates the virtual surface, such as at an outer edge of the virtual surface. For example, assuming the modeled shape and pose of the tool are the same during penetration, the entire tool may be over the virtual surface in one situation, and the tool may overhang the outer edge of the virtual surface in another situation. In such situations, conventional surface modeling again applies the same counter force based simply on the linear depth of penetration without taking into account how much of the tool is engaging the virtual surface.

As such, there is a need in the art for systems and methods for addressing at least the aforementioned problems.

SUMMARY

One example of a robotic system is provided. The robotic system comprises a tool and a manipulator comprising a plurality of links and configured to move the tool. A controller is coupled to the manipulator and configured to implement a virtual simulation wherein the tool is represented as a virtual volume. The virtual volume is configured to interact relative to a virtual boundary defined by a mesh of polygonal elements. The controller is configured to compute a reactive force in response to penetration of one of the polygonal elements by the virtual volume in the virtual simulation. The reactive force is computed based on a penetration factor being a function of a geometry of the virtual volume bound relative to a geometry of the polygonal element. The controller is configured to apply the reactive force to the virtual volume in the virtual simulation to reduce penetration of the polygonal element by the virtual volume. The controller commands the manipulator to move the tool in accordance with application of the reactive force to the virtual volume in the virtual simulation to constrain movement of the tool relative to the virtual boundary.

One example of a method of controlling a robotic system is provided. The robotic system comprises a tool, a manipulator comprising a plurality of links and configured to move the tool, and a controller coupled to the manipulator and configured to implement a virtual simulation. The tool is represented as a virtual volume being configured to interact relative to a virtual boundary. The virtual boundary is defined by a mesh of polygonal elements. The method comprises the controller computing a reactive force in response to penetration of one of the polygonal elements by the virtual volume in the virtual simulation. The reactive force is computed based on a penetration factor being a function of a geometry of the virtual volume bound relative to a geometry of the polygonal element. The method comprises the controller applying the reactive force to the virtual volume in the virtual simulation for reducing penetration of the polygonal element by the virtual volume. The controller commands the manipulator for moving the tool in accordance with application of the reactive force to the virtual volume in the virtual simulation for constraining movement of the tool relative to the virtual boundary.

One example of a controller-implemented method of simulating dynamics of a tool of a robotic system is provided. The method comprises simulating the tool as a virtual volume and simulating a virtual boundary comprising a mesh of polygonal elements. Movement of the virtual volume is simulated to penetrate multiple polygonal elements simultaneously. The method comprises computing multiple reactive forces in response to simultaneous penetration of the multiple polygonal elements. Each reactive force is computed based on a penetration factor being a function of a geometry of the virtual volume bound relative to a geometry of each polygonal element. The method comprises combining the multiple reactive forces for generating a combined reactive force. A weighting factor is applied to each of the reactive forces such that the combined reactive force is constant for any given simultaneous penetration of multiple polygonal elements by the virtual volume. Application of the combined reactive force is simulated to the virtual volume.

The robotic system and methods advantageously compute the reactive force related based as a function of a geometry of the virtual volume bound relative to a geometry of the polygonal element. In so doing, the reactive force provides a natural reactive force to movement of the tool for any given situation accounting for complexities of the virtual boundary, number of polygonal elements penetrated, modeled shapes of the tool as the virtual volume, and/or poses of the tool during penetration.

In turn, when the tool attempts to penetrate the virtual boundary, and in particular, when the tool simultaneously penetrates multiple polygonal elements, the manipulator moves the tool in a manner to provide consistent and expected movement of the tool responsive to the reactive forces.

The techniques described herein further account for situations where the linear depth of penetration (i.e., the distance by which the virtual volume protrudes into the polygonal element and/or virtual boundary) is the same, yet the cross sectional area or displaced volume of the virtual volume and/or virtual boundary is different. The reactive forces are different when computed as function of a geometry of the virtual volume because the reaction forces account more accurately account for a magnitude of penetration by the geometry of virtual volume. The penetration factor does not change linearly with respect to linear depth of penetration because the penetrating body is volumetric and does not apply a linear impact force to the polygonal element and/or virtual boundary. Instead, the penetrating body applies an impact force as a higher order function related to the volumetric shape of the virtual volume. Accordingly, the penetration factor changes with respect to linear depth of penetration according to this higher order volumetric function. Said differently, the penetration factor takes into account the displaced volume or penetrating volume of the virtual boundary or virtual volume.

Moreover, at an outer edge of the virtual boundary, for example, wherein in one situation the entire tool may be over the virtual boundary and in another situation a portion of the tool overhangs the outer edge of the virtual boundary (assuming the same virtual volume and the same pose of the virtual volume during penetration), the techniques described herein are likely to generate different reactive forces because the penetration factor more accurately accounts for how much of the virtual volume is engaging the virtual boundary.

The techniques further provide a smoother response to opposing the virtual boundary at non-planar polygonal elements of the virtual boundary, such as corners, peaks, valleys, etc. For example, the techniques provide gradual increase in reactive force to avoid discrete jumps in reactive force that may move the tool abruptly or unnaturally during encounters with such non-planar polygonal elements. For example, as the tool rolls over an outside corner defined by the virtual boundary, the penetration factors are more likely to offset, thereby providing combined reactive forces that are substantially consistent. This eliminates any force spikes applied to the tool while rolling over such corners. The reactive response is smooth even though penetration by the virtual volume may occur with respect to more than one polygonal element, and even at the same linear depth. In turn, unexpected kick back of the tool while rolling over the non-planar polygonal elements is mitigated. Thus, the techniques described herein solve surface modeling issues relating to non-planar polygonal elements.

Of course, depending on various configurations and situations experienced, the robotic system and method may exhibit advantages and provide technical solutions other than those described herein.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Overview of Robotic System

Referring to the Figures, wherein like numerals indicate like or corresponding parts throughout the several views, a robotic system 10 (hereinafter "system") and methods for operating the system 10 are shown throughout.

Figure 1:
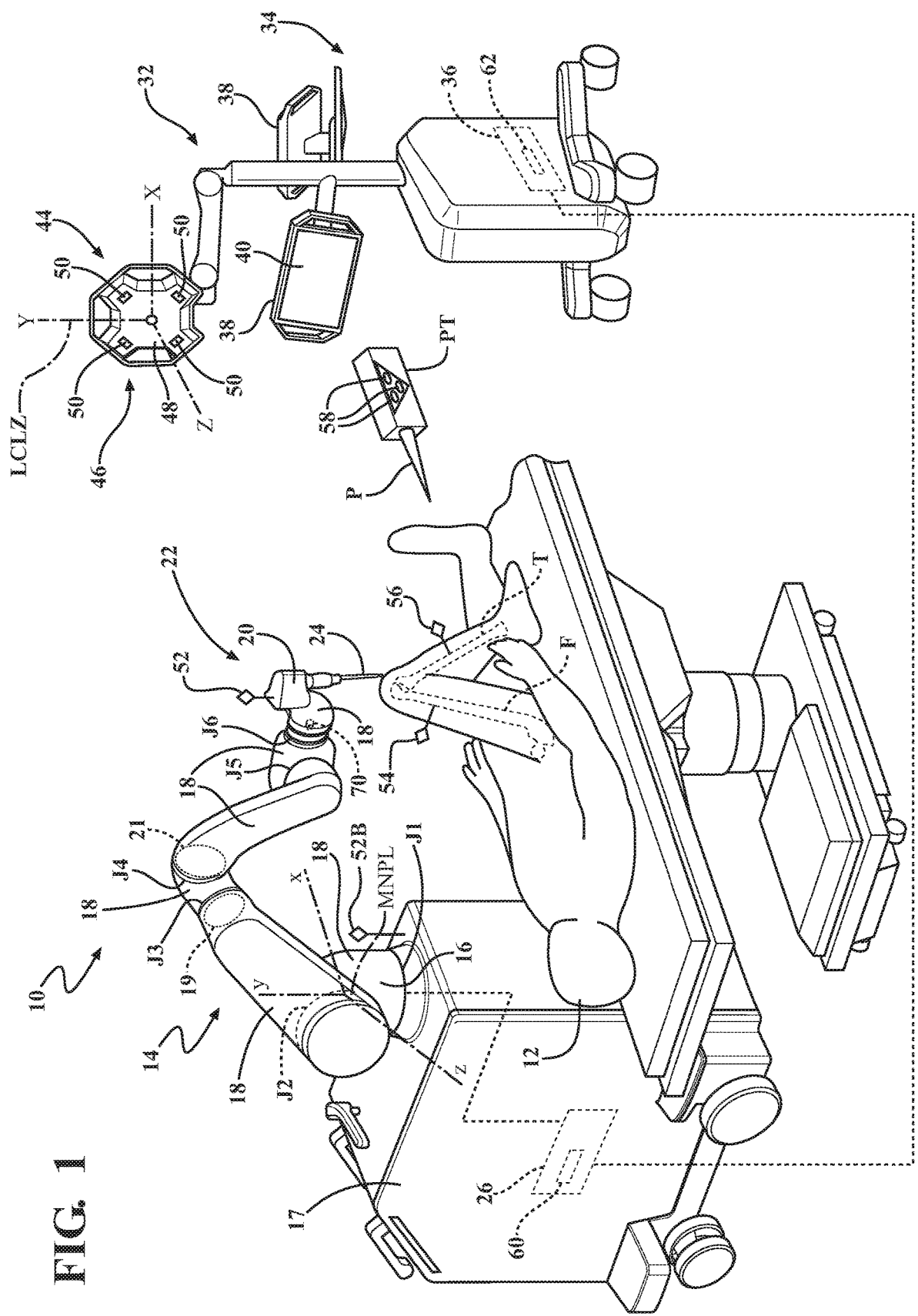
FIG. 1 is a perspective view of a robotic system, according to one example.

As shown in FIG. 1, the system 10 is a robotic surgical system for treating an anatomy of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants including unicompartmental, bicompartmental, multicompartmental, total knee implants, or spinal related applications. Some of these types of implants are shown in U.S. Patent Application Publication No. 2012/0030429, entitled, "Prosthetic Implant and Method of Implantation," the disclosure of which is hereby incorporated by reference. Those skilled in the art appreciate that the system 10 and method disclosed herein may be used to perform other procedures, surgical or non-surgical, or may be used in industrial applications or other applications where robotic systems are utilized.

The system 10 includes a manipulator 14. In one example, the manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1) or a parallel arm configuration. In other examples, more than one manipulator 14 may be utilized in a multiple arm configuration.

The manipulator 14 comprises a plurality of joints (J). Each pair of adjacent links 18 is connected by one of the joints (J). The manipulator 14 according to one example has six joints (J1-J6) implementing at least six-degrees of freedom (DOF) for the manipulator 14. However, the manipulator 14 may have any number of degrees of freedom and may have any suitable number of joints (J) and redundant joints (J).

A plurality of position sensors 19 are located at the joints (J) for determining position data of the joints (J). For simplicity, only one position sensor 19 is illustrated in FIG. 1, although it is to be appreciated that the other position sensors 19 may be similarly illustrated for other joints (J). One example of the position sensor 19 is an encoder that measures the joint angle of the respective joint (J).

At each joint (J), there is an actuator, such as a joint motor 21 disposed between the adjacent links 18. For simplicity, only one joint motor 21 is shown in FIG. 1, although it is to be appreciated that the other joint motors 21 may be similarly illustrated. Each joint (J) is actively driven by one of the joint motors 21. The joint motors 21 are configured to rotate the links 18. As such, positions of the links 18 are set by joint motors 21.

Each joint motor 21 may be attached to a structural frame internal to the manipulator 14. In one example, the joint motor 21 is a servo motor, such as a permanent magnet brushless motor. However, the joint motor 21 may have other configurations, such as synchronous motors, brush-type DC motors, stepper motors, induction motors, and the like.

The joint motors 21 are positionable at one of a plurality of angular positions, hereinafter referred to as joint angles. The joint angle is the angle of the joint (J) between adjacent links 18. In one example, each joint motor 21 may be equipped with one of the position sensors 19. Alternatively, each link 18 being driven by that particular joint motor 21 may be equipped with the position sensor 19. In some examples, two position sensors 19, one for the joint motor 21 and one for the link 18 being moved can be used to determine the joint angle, such as by averaging the joint angle, and the displacement between motor 21 and joint (J) through compliant transmission.

Each joint (J) is configured to undergo a joint torque. The joint torque is a turning or twisting "force" of the joint (J) and is a function of the force applied at a length from a pivot point of the joint (J). A torque sensor 27 (FIG. 3) may be connected to one or more joint motors 21 for measuring the joint torque of the joint (J). Alternatively, signals representative of currents applied to the joint motors 21 may be analyzed by a controller to measure the joint torques.

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of the manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference point, which does not move in the manipulator coordinate system MNPL.

A tool 20 couples to the manipulator 14 and is movable by the manipulator 14. Specifically, the manipulator 14 moves one or more of the joints J1-J6 of the links 18 to move the tool 20 relative to the base 16. The tool 20 is or forms part of an end effector 22. The tool 20 interacts with the anatomy in certain modes and may be grasped by the operator in certain modes. One exemplary arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The tool 20 can be like that shown in U.S. Patent Application Publication No. 2014/0276949, filed on Mar. 15, 2014, entitled, "End Effector of a Surgical Robotic Manipulator," hereby incorporated by reference. The tool 20 may be a surgical configured to manipulate the anatomy of the patient, or may be any other type of tool (surgical or non-surgical) employed by the manipulator 14. The manipulator 14 and the tool 20 may be arranged in configurations other than those specifically described herein.

In one example, the tool 20 includes an energy applicator 24 designed to contact the tissue of the patient 12 at the surgical site. The energy applicator 24 may be a drill, a saw blade, a bur, an ultrasonic vibrating tip, or the like. The tool 20 may comprise a tool center point (TCP), which in one example, is a predetermined reference point defined at the energy applicator 24. The TCP has known position in its own coordinate system. In one example, the TCP is assumed to be located at the center of a spherical feature of the tool 20 such that only one point is tracked. The TCP may relate to a bur having a specified diameter. In other examples, the tool 20 may be a probe, cutting guide, guide tube, or other type of guide member for guiding a hand-held tool with respect to the anatomy.

Figure 2:
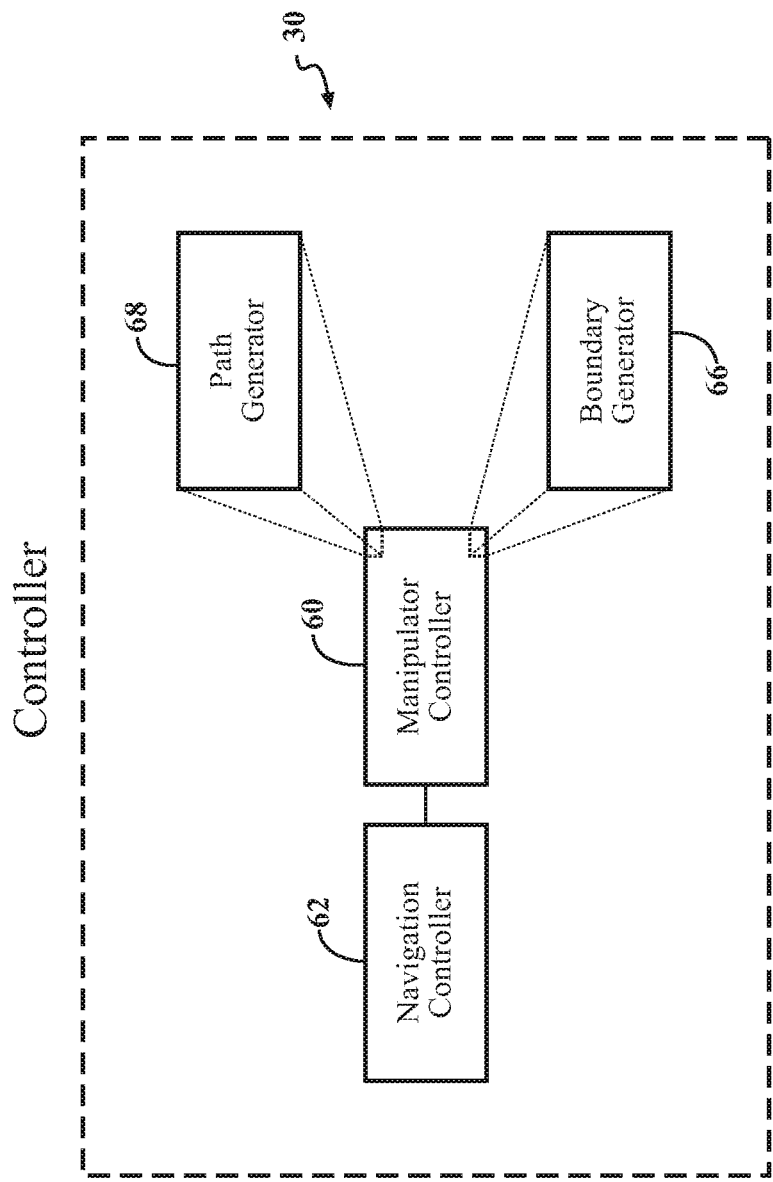
FIG. 2 is a block diagram of one example of a controller of the robotic system.

Referring to FIG. 2, the system 10 includes a controller 30 coupled to the manipulator 14. The controller 30 includes software and/or hardware for controlling the manipulator 14 for moving the tool 20. The controller 30 directs the motion of the manipulator 14 and controls a state (position and/or orientation) of the tool 20 with respect to a coordinate system. In one example, the coordinate system is the manipulator coordinate system MNPL, as shown in FIG. 1. The manipulator coordinate system MNPL has an origin located at any suitable pose with respect to the manipulator 14. Axes of the manipulator coordinate system MNPL may be arbitrarily chosen as well. Generally, the origin of the manipulator coordinate system MNPL is defined at the fixed reference point of the base 16. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

As shown in FIG. 1, the system 10 may further include a navigation system 32. The navigation system 32 is configured to track movement of various objects. Such objects include, for example, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein. One example of the navigation system 32 is described in U.S. Pat. No. 9,008,757, filed on Sep. 24, 2013, entitled, "Navigation System Including Optical and Non-Optical Sensors," hereby incorporated by reference.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. An input device 40 may be used to input information into the navigation computer 36 or otherwise to select/control certain aspects of the navigation computer 36. As shown in FIG. 1, the input device 40 includes an interactive touchscreen display. However, the input device 40 may include any one or more of a keyboard, a mouse, a microphone (voice-activation), gesture control devices, and the like. The manipulator 14 and/or manipulator cart 17 house a manipulator computer 26, or other type of control unit. The controller 30 may be implemented on any suitable device or devices in the system 10, including, but not limited to, the manipulator computer 26, the navigation computer 36, and any combination thereof.

The navigation system 32 may also include a navigation localizer 44 (hereinafter "localizer") that communicates with the navigation computer 36. In one example, the localizer 44 is an optical localizer and includes a camera unit 46. The camera unit 46 has an outer casing 48 that houses one or more optical sensors 50.

In the illustrated example of FIG. 1, the navigation system 32 includes one or more trackers. In one example, the trackers include a pointer tracker PT, a tool tracker 52, a first patient tracker 54, and a second patient tracker 56. In FIG. 1, the tool tracker 52 is firmly attached to the tool 20, the first patient tracker 54 is firmly affixed to the femur F of the patient 12, and the second patient tracker 56 is firmly affixed to the tibia T of the patient 12. In this example, the patient trackers 54, 56 are attached to sections of bone. The pointer tracker PT is attached to a pointer P used for registering the anatomy to the localizer coordinate system LCLZ. Those skilled in the art appreciate that the trackers 52, 54, 56, PT may be fixed to their respective components in any suitable manner. Additionally, the navigation system 32 may include trackers for other components of the system, including, but not limited to, the base 16 (tracker 52B), the cart 17, and any one or more links 18 of the manipulator 14.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the tool 20, the femur (F) and the tibia (T). The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the navigation system 32 is shown in the Figures, the navigation system 32 may have any other suitable configuration for tracking the tool 20 and the patient 12. In one example, the navigation system 32 and/or localizer 44 are ultrasound-based. For example, the navigation system 32 may comprise an ultrasound imaging device coupled to the navigation computer 36. The ultrasound imaging device images any of the aforementioned objects, e.g., the tool 20 and the patient 12 and generates state signals to the controller 30 based on the ultrasound images. The ultrasound images may be 2-D, 3-D, or a combination of both. The navigation computer 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF) based. For example, the navigation system 32 may comprise an RF transceiver in communication with the navigation computer 36. Any of the tool 20 and the patient 12 may comprise RF emitters or transponders attached thereto. The RF emitters or transponders may be passive or actively energized. The RF transceiver transmits an RF tracking signal and generates state signals to the controller 30 based on RF signals received from the RF emitters. The navigation computer 36 and/or the controller 30 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another example, the navigation system 32 and/or localizer 44 are electromagnetically based. For example, the navigation system 32 may comprise an EM transceiver coupled to the navigation computer 36. The tool 20 and the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the controller 30 based upon EM signals received from the trackers. The navigation computer 36 and/or the controller 30 may analyze the received EM signals to associate relative states thereto. Again, such navigation system 32 examples may have structural configurations that are different than the navigation system 32 configuration as shown throughout the Figures.

Those skilled in the art appreciate that the navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

Examples of software modules of the controller 30 are shown in FIG. 2. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

As shown in FIGS. 1 and 2, the controller 30 includes a manipulator controller 60 configured to process data to direct motion of the manipulator 14. In one example, as shown in FIG. 1, the manipulator controller 60 is implemented on the manipulator computer 26. The manipulator controller 60 may receive and process data from a single source or multiple sources. The controller 30 may further include a navigation controller 62 for communicating the state data relating to the femur F, tibia T, and/or tool 20 to the manipulator controller 60. The manipulator controller 60 receives and processes the state data provided by the navigation controller 62 to direct movement of the manipulator 14. In one example, as shown in FIG. 1, the navigation controller 62 is implemented on the navigation computer 36. The manipulator controller 60 and/or navigation controller 62 may also communicate states of the patient 12 and/or tool 20 to the operator by displaying an image of the femur F and/or tibia T and the tool 20 on the one or more displays 38. The manipulator computer 26 or navigation computer 36 may also command display of instructions or request information using the display 38 to interact with the operator and for directing the manipulator 14.

As shown in FIG. 2, the controller 30 includes a boundary generator 66. The boundary generator 66 is a software module that may be implemented on the manipulator controller 60. Alternatively, the boundary generator 66 may be implemented on other components, such as the navigation controller 62.

Figure 4:
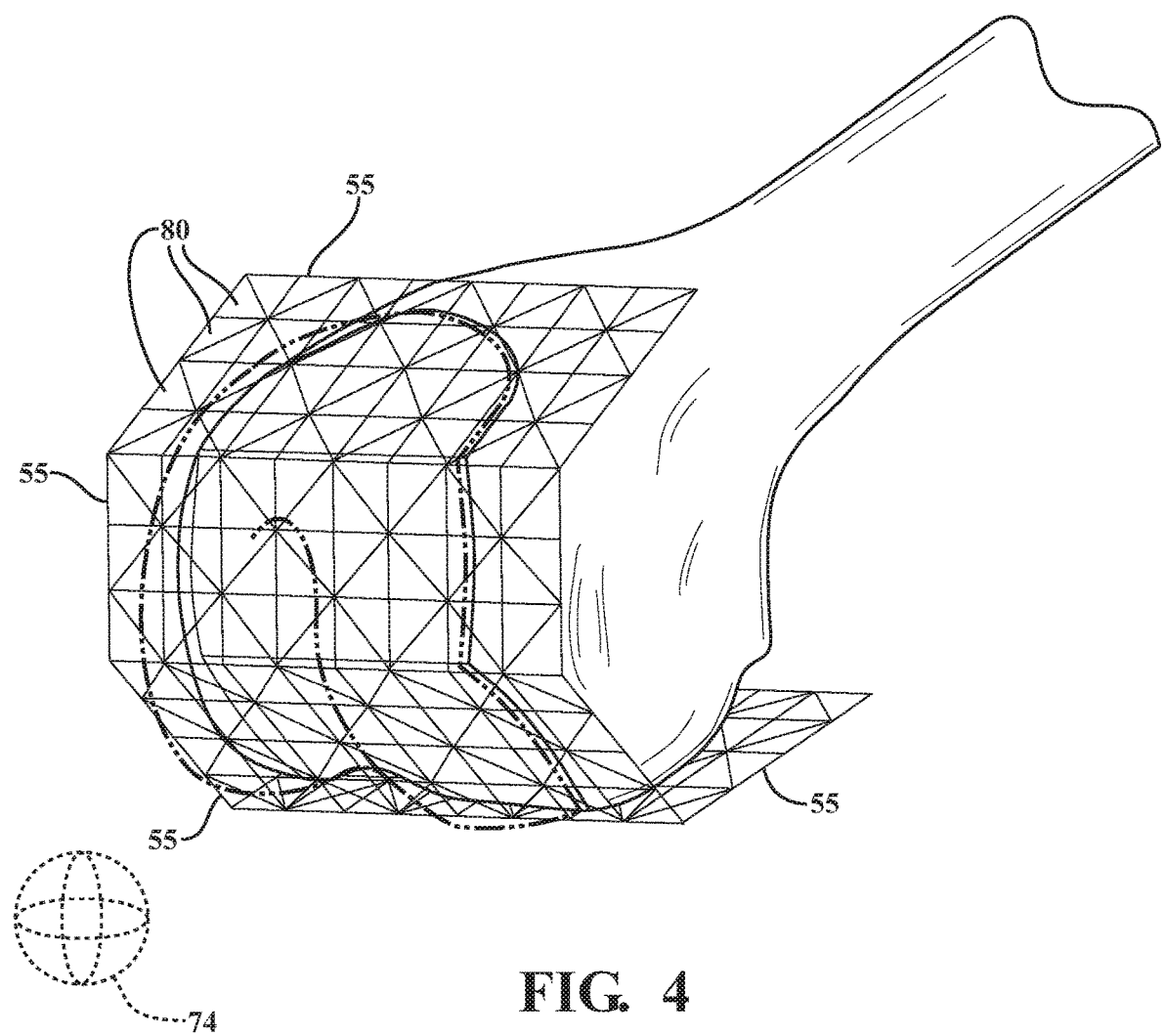
FIG. 4 is an example of a simulated virtual volume representative of a tool of the manipulator and wherein the virtual volume is configured to interact relative to a virtual boundary that is associated with the anatomy and comprises a mesh of polygonal elements.

The boundary generator 66 generates one or more virtual boundaries 55 for constraining the tool 20, as shown in FIG. 4. In situations where the tool 20 interacts with a target site of the anatomy, the virtual boundaries 55 may be associated with the target site, as shown in FIG. 4. The virtual boundaries 55 may be defined with respect to a 3-D bone model registered to actual anatomy such that the virtual boundaries 55 are fixed relative to the bone model. In this situation, the virtual boundaries 55 delineate tissue that should be removed from tissue that should not be removed. In some instances, the state of the tool 20 may be tracked relative to the virtual boundaries 55 using the navigation system 32 which tracks the states of the tool 20 (e.g., using tool tracker 52) and states of the anatomy (e.g., using patient trackers 54, 56). In one example, the state of the TCP of the tool 20 is measured relative to the virtual boundaries 55 for purposes of determining when and where reactive forces should be applied to the manipulator 14, or more specifically, the tool 20. Additional detail regarding the virtual boundaries 55 and such reactive forces are described below. One exemplary system and method for generating virtual boundaries 55 relative to the anatomy and controlling the manipulator 14 in relation to such virtual boundaries 55 is explained in U.S. Provisional Patent Application No. 62/435,254, filed on Dec. 16, 2016 and entitled, "Techniques for Modifying Tool Operation in a Surgical Robotic System Based on Comparing Actual and Commanded states of the Tool Relative to a Surgical Site," the disclosure of which is hereby incorporated by reference.

In another example, the navigation system 32 is configured to track states of an object to be avoided by the tool 20 and the virtual boundary 55 is associated with the object to be avoided. The object to be avoided may be any object in the sterile field with which the tool 20 may inadvertently interact. Such objects include, but are not limited to, parts of the patient other than the surgical site, surgical personnel, leg holders, suction/irrigation tools, patient trackers 54, 56, retractors, other manipulators 14, lighting equipment, or the like. One exemplary system and method for generating virtual boundaries 55 relative to objects to be avoided and controlling the manipulator 14 in relation to such virtual boundaries 55 is explained in U.S. Patent Application Publication No. 2014/0276943, filed on Mar. 12, 2014 and entitled, "Systems and Methods for Establishing Virtual Constraint Boundaries," the disclosure of which is hereby incorporated by reference.

The controller 30, and more specifically, the manipulator controller 60, may execute another software module providing a tool path generator 68, as shown in FIG. 2. The tool path generator 68 generates a path for the tool 20 to traverse, such as for removing sections of the anatomy to receive an implant. One exemplary system and method for generating the tool path is explained in U.S. Pat. No. 9,119,655, entitled, "Surgical Manipulator Capable of Controlling a Surgical Instrument in Multiple Modes," the disclosure of which is hereby incorporated by reference.

In some examples, the virtual boundaries 55 and/or tool paths may be generated offline rather than on the manipulator computer 26 or navigation computer 36. Thereafter, the virtual boundaries 55 and/or tool paths may be utilized at runtime by the manipulator controller 60.

As shown in FIG. 1, a sensor 70, such as a force-torque sensor, may be coupled to the manipulator 14. Specifically, the force-torque sensor 70 may be mounted between the distal link 18 and the tool 20. The force-torque sensor 70 is configured to output variable signals as a function of forced and/or torques to which the tool 20 is exposed as the operator grasps the tool 20. By doing so, the force-torque sensor 70 allows sensing of input forces and/or torques applied to the tool 20. As will be described below, the input force and/or torque is utilized to control movement of the manipulator 14. In one example, the force-torque sensor 70 is a 6DOF sensor such that the force-torque sensor 70 is configured to output signals representative of three mutually orthogonal forces and three torques about the axes of the orthogonal forces that are applied to the tool 20. Additionally or alternatively, the input force and/or torque applied to the tool 20 may be determined using joint torques, as is described in detail below.

Figure 3:
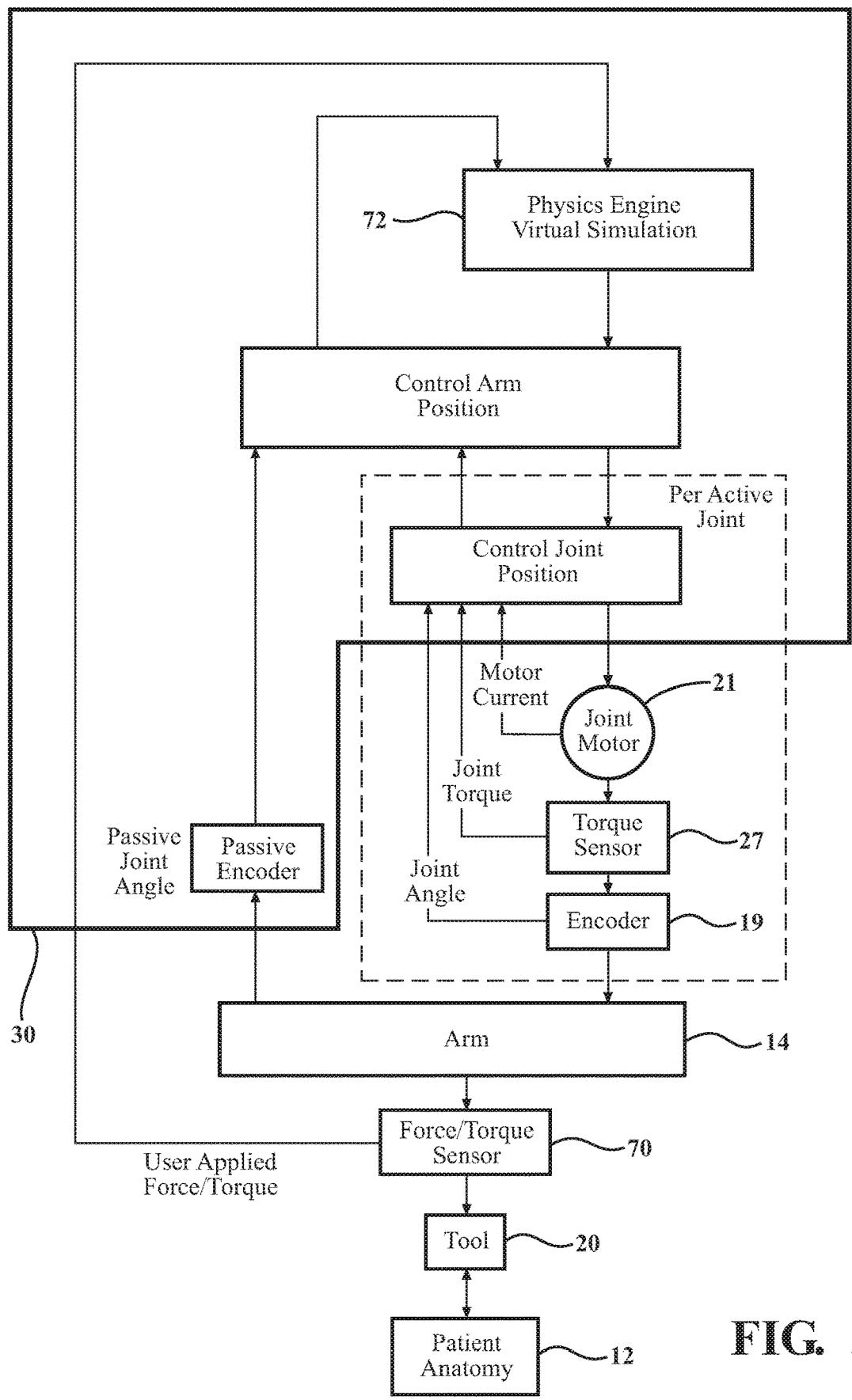
FIG. 3 is a block diagram of control loops implemented by the controller and a manipulator of the robotic system.

As shown in FIG. 3, the controller 30 is in communication with the joint motors 21 for commanding movement and position of the links 18. The controller 30 is further coupled to the position sensors (e.g., encoders) 19 and is configured to measure an actual joint angle of each respective joint (J) using signals received from the position sensors 19. The controller 30 commands the joint motors 21, such as through a joint motor sub-controller, to move to a commanded joint angle. The controller 30 may receive signals indicative of the measured joint torque of the joint (J) from the torque sensor(s) 28 at the joint motors 21. The controller 30 further is coupled to the force-torque sensor 70 for receiving signals indicative of the input force and/or torque applied to the tool 20.

II. Admittance Control and Virtual Simulation

In one example, the controller 30 is an admittance-type controller. In other words, the controller 30 determines control forces and/or torques and commands position of the manipulator 14. Examples of the control forces and/or torques are described below. In one example, the controller 30 includes solely a single admittance controller such that control forces and/or torques are determined and analyzed solely by the single controller 30 to determine the force. In other words, in this example, separate admittance controllers for different control forces and/or torques are not utilized. In other examples, additional controllers may be used.

Using admittance control, the techniques described herein may, at times, give the impression that some of the joints (J) are passive, meaning that the joint (J) is moved directly by the force exerted by the user (similar to a door joint). However, in the examples described the joints (J) are actively driven. The system 10 and method mimic passive behavior by actively driving the joints (J) and thereby commanding control of the manipulator 14 in response to determined control forces and/or torques.

To execute force determinations with admittance control, the controller 30 is configured to implement a virtual simulation 72, as represented in FIG. 3. The controller 30 simulates dynamics of the tool 20 in the virtual simulation 72. In one example, the virtual simulation 72 is implemented using a physics engine, which is executable software stored in a non-transitory memory of any of the aforementioned computers 26, 36 and implemented by the controller 30.

For the virtual simulation, the controller 30 models the tool 20 as a virtual rigid body (as shown in FIG. 4, for example). The virtual rigid body is a dynamic object and a rigid body representation of the tool 20 for purposes of the virtual simulation 72. The virtual rigid body is free to move according to 6DOF in Cartesian task space according to the virtual simulation 72. Specific examples of the virtual rigid body are described in the subsequent section.

The virtual simulation 72 and the virtual rigid body may be simulated and otherwise processed computationally without visual or graphical representations. Thus, it is not required that the virtual simulation 72 virtually display dynamics the virtual rigid body. In other words, the virtual rigid body need not be modeled within a graphics application executed on a processing unit. The virtual rigid body exists only for the virtual simulation 72.

In some instances, simulated movement of a virtual tool, which is tracked to the actual tool 20, may be displayed at the surgical site to provide visual assistance during operation of the procedure. However, in such instances, the displayed tool is not directly a result of the virtual simulation 72.

The tool 20 may be modeled as the virtual rigid body according to various methods. For example, the virtual rigid body may correspond to features, which may be on or within the tool 20. Additionally or alternatively, the virtual rigid body may be configured to extend, in part, beyond the tool 20. The virtual rigid body may take into account the end effector 22 as a whole (including the tool 20 and the energy applicator 32) or may take into account the tool 20 without the energy applicator 32. Furthermore, the virtual rigid body may be based on the TCP. In yet another example, the virtual rigid body is based on a range of motion of the tool 20, rather than a static position of the tool 20. For example, the tool 20 may comprise sagittal saw blade that is configured to oscillate between two end points. The virtual rigid body may be statically defined to include the two end points and any appropriate space in between these two end points to account for the full range of motion of the tool 20 in relation to the virtual boundary 55. Similar modeling techniques for tools 20 that effect a range of motion may be utilized other than those described above for the sagittal saw.

In one example, the virtual rigid body is generated about a center of mass of the tool 20. Here "center of mass" is understood to be the point around which the tool 20 would rotate if a force is applied to another point of the tool 20 and the tool 20 were otherwise unconstrained, i.e., not constrained by the manipulator 14. The center of mass of the virtual rigid body may be close to, but need not be the same as, the actual center of mass of the tool 20. The center of mass of the virtual rigid body can be determined empirically. Once the tool 20 is attached to the manipulator 14, the position of the center of mass can be reset to accommodate the preferences of the individual practitioners. In other examples, the virtual rigid body may correspond to other features of the tool 20, such as the center of gravity, or the like.

The controller 30 effectively simulates rigid body dynamics of the tool 20 by virtually applying control forces and/or torques to the virtual rigid body. As shown in FIG. 3, the control forces and/or torques applied to the virtual rigid body may be user applied (as detected from the force/torque sensor 70) and/or based on other behavior and motion control forces and/or torques. These control forces and/or torques are applied, in part, to control joint (J) position and may be derived from various sources. One of the control forces and/or torques may be a reactive force (Fr) responsive to interaction of the tool 20 with the virtual boundaries produced by the boundary generator 68. Techniques for generating these reactive forces (Fr) are the primary subject of the subsequent section and are described in detail below.

Additionally, control forces and/or torques may be applied to constrain movement of the tool 20 along the tool path provided from the path generator 68. These control forces and/or torques may be applied to constrain orientation of the tool 20 further within an acceptable range of orientations along the tool path. Backdrive control forces indicative of a disturbance along the tool path (e.g., based on external forces applied to the manipulator 14) also may be applied to the virtual rigid body. Control forces and/or torques may be applied to the virtual rigid body to overcome the force of gravity. Other control forces that may applied to the virtual rigid body include, but are not limited to forces to avoid joint limits, forces to avoid singularities between links 18 of the manipulator 14, forces to maintain the tool 20 within a workspace boundary of the manipulator 14, and the like.

These various control forces and/or torques to apply to the virtual rigid body are detected and/or determined by the controller 30 and are inputted into a system of equations that the controller 30 solves in order to provide a kinematic solution satisfying the system of equations (i.e., satisfying the various control forces and/or torques and any applicable constraints). The controller 60 may be configured with any suitable algorithmic instructions (e.g., such as an iterative constraint solver) to execute this computation. This operation is performed in the virtual simulation 72 in order to determine the next commanded position of the manipulator 14. The virtual simulation 72 simulates rigid body dynamics of the tool 20 before such dynamics of the tool 20 are physically performed during positioning of the manipulator 14.

Understood differently, the virtual rigid body is in a first pose at commencement of each iteration of the virtual simulation 72. The controller 30 inputs the control forces and/or torques into the virtual simulation 72 and these control forces and/or torques are applied to the virtual rigid body in the virtual simulation 72 when the virtual rigid body is in the first pose. The virtual rigid body is moved to a subsequent pose having a different state (i.e., position and/or orientation) within Cartesian space in response to the controller 30 satisfying the inputted control forces and/or torques.

In one example, the virtual rigid body does not actually move during simulation. In other words, the control forces and/or torques are inputted into the system of equations and solved computationally. Each solved equation may indicate theoretical movement of the virtual rigid body according to the respective control force(s) for the equations. In other words, anticipated movement of the virtual rigid body in accordance with each applied control force and/or torque is taken into account.

Additionally or alternatively, the virtual rigid body moves in the virtual simulation 72 during solving of the system of equations. In other words, the virtual rigid body is moved in accordance with the applied control forces and/or torques during the process of solving the system of equations. The virtual rigid body may move to the subsequent pose in the virtual simulation 72 after the system of equations are solved. However, even this subsequent pose may be represented strictly in a computational sense such that movement of the virtual rigid body from the first pose to the second pose does not occur.

Knowing the subsequent pose of the virtual rigid body based on the virtual simulation 72, the controller 30 is configured to command action of the joints (J) in accordance with the virtual simulation 72. That is, the controller 30 converts the dynamics of the virtual rigid body in Cartesian space to direct motion of the manipulator 14 and to control the state of the tool 20 in joint space. For instance, forces resulting in the subsequent pose are applied to a Jacobian calculator, which calculates Jacobian matrices relating motion within Cartesian space to motion within joint space.

In one example, the controller 30 is configured to determine the appropriate joint angles to command for the joints (J) based on the output of the virtual simulation 72. That is, the controller 30 computes the commanded joint angle for each of the joints (J). From here, the controller 30 regulates the joint angle of each joint (J) and continually adjusts the torque that each joint motor 21 outputs to, as closely as possible, ensure that the joint motor 21 drives the associated joint (J) to the commanded joint angle. The controller 30 is configured to apply signals to each joint motor 21 so that each joint motor 21 drives the associated joint (J) to the commanded joint angle. The controller 30 may use any suitable position control algorithms for controlling positioning the joints (J) based on the commanded joint angles. The controller 30 may generate the commanded joint angle only for those joints (J) that are active, i.e., expected to move based on the output of the virtual simulation 72.

In some examples, as represented in FIG. 3, the controller 30 generates the commanded joint angle for each of the joints (J) separately and individually (e.g., per each active joint). For example, the joints (J) may be considered in succession such that the commanded joint angle for J1 is generated first, and the commanded joint angle for J6 is generated last, or vice-versa.

III. Techniques for Computing Reactive Forces Based on Penetration Factors to Implement Virtual Boundaries.

Referring now to FIGS. 4-18, described herein are techniques for generating reactive forces (Fr) that are applied to the virtual rigid body in the virtual simulation 72 responsive to interaction of the tool 20 with the virtual boundaries 55, e.g., in the manipulator coordinate system MNPL. In accordance with application of the reactive forces (Fr) to the virtual volume 74 in the virtual simulation 72, the controller 30 commands the manipulator 14 to move the tool 20 to constrain movement of the tool 20 relative to the virtual boundary 55. Details regarding configurations and functions of the virtual rigid body and the virtual boundaries 55, as well as techniques for computing the reactive forces (Fr) are also provided below. The methods for implementing these techniques are fully understood through any functional description of the elements described herein.

To implement the techniques described herein for computing the reactive forces (Fr), the virtual rigid body is defined as a virtual volume 74, as shown in FIG. 4. Thus, the virtual rigid body is a three-dimensionally modeled object, rather than a single point or 2D planar element. Features, functionality, and configurations of the virtual rigid body described in the previous section should be understood to apply to virtual volume 74 described in this section. As will be apparent based on the techniques described below, providing the virtual rigid body as the virtual volume 74 enables more precise dynamic interaction between the virtual volume 74 and the virtual boundaries 55, as compared with a two-dimensional or single dimensional rigid body.

The virtual volume 74 may have various configurations. In one example, the virtual volume 74 comprises a single face, zero edges, and zero vertices. For instance, as shown in FIGS. 4-18, the virtual volume 74 is a sphere. The virtual volume 74 may be other shapes having single face, zero edges, and zero vertices, such as a spheroid (prolate or oblate), an ellipsoid, a toroid (e.g., a doughnut shape), or any combination thereof. By having the single face, zero edges, and zero vertices, the entire virtual volume 74 is provided with a smooth surface. As will be apparent based on the techniques described below, reactive forces (Fr) computed in response to interaction of the single face virtual volume 74 with the virtual boundary 55 are likely to provide responses that more accurately reflect interaction as compared with reactive forces (Fr) computed in response to interaction of the virtual boundary 55 by volumes having a greater number of faces.

It is possible to implement the techniques described herein with the virtual volume 74 having more than one face. For instance, the virtual volume 74 may be a cone, a semi-sphere, or any of the aforementioned volumes (i.e., spheres, spheroids ellipsoids, toroids), wherein the virtual volume 74 has a high resolution of faces thereby mimicking the single-faced and smooth version of the respective volume. Other examples of the virtual volume 74 are contemplated in view of the teachings of the techniques provided herein.

One example of the virtual boundary 55 is shown in FIG. 4. Of course, any number of virtual boundaries 55 may be utilized. The virtual boundaries 55 may be spaced apart and separated from one another or may be integrally connected to one another. The virtual boundaries 55 may be planar or may be defined by more complex shapes, such as polyhedrons, or the like.

As shown in FIG. 4, the virtual boundaries 55 are defined by a mesh of polygonal elements 80. The mesh is formed of multiple polygonal elements 80 being disposed adjacent to one another and having adjacent vertices and edges aligned with one other.

Each polygonal element 80 may be formed of any polygon having a plane figure with at least three straight sides and angles. Ideally, the polygon sides enable the mesh to be formed without any gaps between adjacent polygonal elements 80. In one example, as shown in FIG. 4, the polygonal elements 80 are triangles. The triangles may be any type, such as equilateral, scalene, isosceles, obtuse, oblique, and/or right. In other examples, the polygonal elements 80 may be quadrilaterals (rectangles, squares), pentagons, hexagons, etc.

Each virtual boundary 55 may comprise the mesh being formed of the same type of polygonal element 80. For instance, in FIG. 4, all the polygonal elements 80 shown are triangles. In other examples, one virtual boundary 55 may comprise the mesh being formed of one type of polygonal element 80 and another virtual boundary 55 may comprise the mesh being formed of another type of polygonal element 80. In yet another example, one virtual boundary 55 may comprise the same mesh being formed by more than one type of polygonal element 80. For instance, groups of each type of polygonal element 50 may be provided for different sections of the same mesh. It is to be appreciated that the virtual boundaries 55, meshes, and polygonal elements 80 may comprise configurations other than those described herein and shown in the Figures.

As described, the virtual volume 74 may interact with, attempt to penetrate, or otherwise penetrate (overshoot) the virtual boundary 55 in accordance with the control forces and/or torques applied to the virtual volume 74 in the virtual simulation 72. When the virtual volume 74 pushes on the virtual boundary 55, the virtual boundary 55 pushes back due to applied compressional impact of the virtual volume 74 and/or the virtual boundary 55. For simplicity, the impact force applied against the virtual boundary 55 by the virtual volume 74 (or vice-versa) is shown in the Figures as ($F_a$). To offset this impact force ($F_a$), the controller 30 generates the reactive force (Fr) to apply to the virtual volume 74, which opposes compression. Thus, the reactive force (Fr) is a component of the system of equations that the controller 30 attempts to satisfy in the virtual simulation 72. Thus, it should be understood that the virtual volume 74 may undergo multiple other control forces and/or torques during the virtual simulation 72 other than the reactive force (Fr). As described, interaction between the virtual volume 74 and the virtual boundary 55 may exist only in a computational sense rather than a graphical sense, by providing parameters and variables of this interaction in the system of equations for solution.

The controller 30 is configured to compute the reactive force (Fr) specifically in response to penetration of one or more of the polygonal elements 80 by the virtual volume 74 in the virtual simulation 72. The reactive force (Fr) is computed based on a penetration factor being a function of a geometry of the virtual volume 74 bound relative to a geometry of the polygonal element 80. As will be apparent from the examples below, the geometry of the virtual volume 74 may be two-dimensional or three-dimensional. The geometry of the virtual volume 74 is bound by the polygonal element 80. For example, the geometry of the virtual volume 74 is bound by a perimeter of the polygonal element 80. In other words, the geometry of the virtual volume 74 for a single polygonal element 80 is considered in as much as the geometry of the virtual volume 74 exists within the perimeter of the polygonal element 80. The various examples of computing penetration factors are described in detail below. These examples may be utilized individually or in combination.

A. Projected Area

In accordance with one example, as shown in FIG. 5-15, the controller 30 is configured to compute the reactive force (Fr) based on the penetration factor being related to a projected area 90 defined by intersection of the virtual volume 74 with the polygonal element 80.

In this example, the term "projected" is a mathematical expression indicating that the area 90 defined by intersection of the virtual volume 74 with the polygonal element 80 is mapped relative to the planar surface of the polygonal element 80. The projected area 90 is also labeled in the Figures as $A_{proj}$. Furthermore, throughout the Figures, the projected area 90 is shown by a shaded region.

The projected area 90 is bound by the polygonal element 80. Specifically, the projected area 90 is bound by a perimeter of the polygonal element 80. In other words, the projected area 90 for a single polygonal element 80 is considered in as much as the projected area 90 exists within the perimeter of the polygonal element 80. Examples where multiple polygonal elements 80 are penetrated by the virtual volume 74 are described below.

As will be apparent from the description and the Figures, the virtual volume 74 is defined such that the projected area 90 changes non-linearly relative to a linear depth of penetration (i.e., the distance by which the virtual volume 74 protrudes into the polygonal element 80 and/or virtual boundary 55) by the virtual volume 74. Although the reactive force (Fr) may change with changes in the linear depth of penetration, the reactive force (Fr) is computed based on the projected area 90 and without computationally accounting for the linear depth of penetration.

As described, the reactive force (Fr) is related to a projected area 90. In one example, the reactive force (Fr) is directly correlated with the projected area 90. Additionally or alternatively, the reactive force (Fr) is proportional to the projected area 90. In one example, the reactive force (Fr) is modeled as a spring with a constant of k. The spring constant k is multiplied by $A_{proj}$ such that $F_R = k\ A_{proj}$. The spring constant k may have any suitable value depending on design configurations reflecting how strongly to oppose penetration of the virtual boundary 55 by the tool 20.

In one example, the reactive force (Fr) is applied as a vector being normal to a plane of the polygonal element 80. The location of the vector with respect to the plane of the polygonal element 80 may vary depending on the location of projected area 90 mapped on to the polygonal element 80. The magnitude of the reactive force (Fr) may vary depending on the size of the projected area 90. The reactive force (Fr) vector may be at an angle that is not normal with respect to the plane of the polygonal element 80 depending on the projected area 90 and/or the pose of the virtual volume 74 during penetration. Techniques for computing the reactive force (Fr) from the projected area 90 are described below.

The controller 30 is configured to apply the reactive force (Fr) to the virtual volume 74 in the virtual simulation 72 to reduce penetration of the polygonal element 80 by the virtual volume 74. Thus, the reactive force (Fr) is configured to offset the impact force ($F_a$) partially or completely. It should be appreciated that the reactive force (Fr) may be applied directly to the virtual volume 74 and/or may be applied to the virtual boundary 55 itself. In either instance, application of the reactive force (Fr) to the virtual volume 74 causes acceleration and a change in the velocity (and hence the pose) of the virtual volume 74 for as long as the virtual volume 74 acts upon the virtual boundary 55. Because the magnitude of impact between the virtual volume 74 and the virtual boundary 55 is likely to occur variably over time, the controller 30 may be configured to generate impulses for minimizing the impact force ($F_a$). Impulses may be generated iteratively to compute the reactive forces (Fr) applied to the virtual volume 74. The impulse is the integral of the reactive force (Fr) over the time. The impulse may be perceived as the effect of the momentary increase of the reactive forces (Fr).

Figure 5:
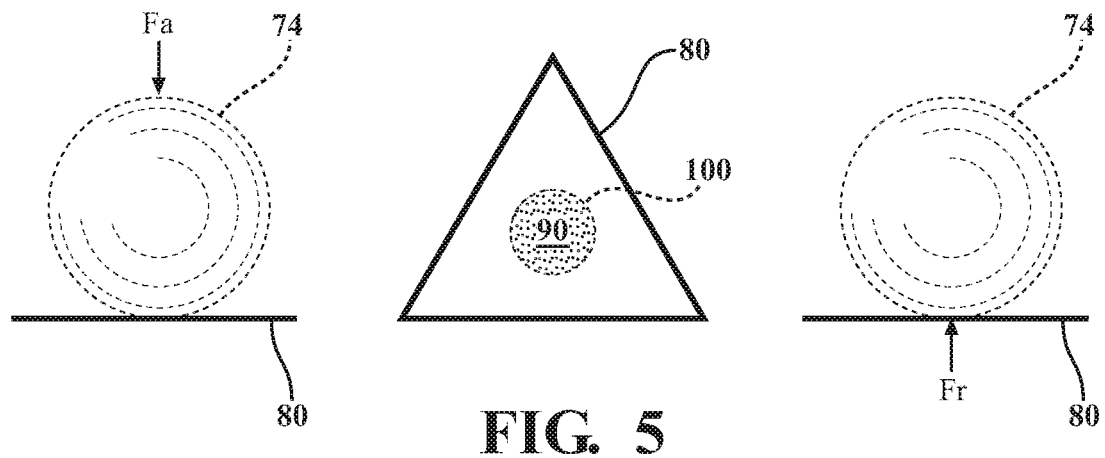
FIG. 5 illustrates one example of using a penetration factor based on projected area to generate a reactive force responsive to interaction of the virtual volume with one polygonal element of the virtual boundary.
Figure 6:
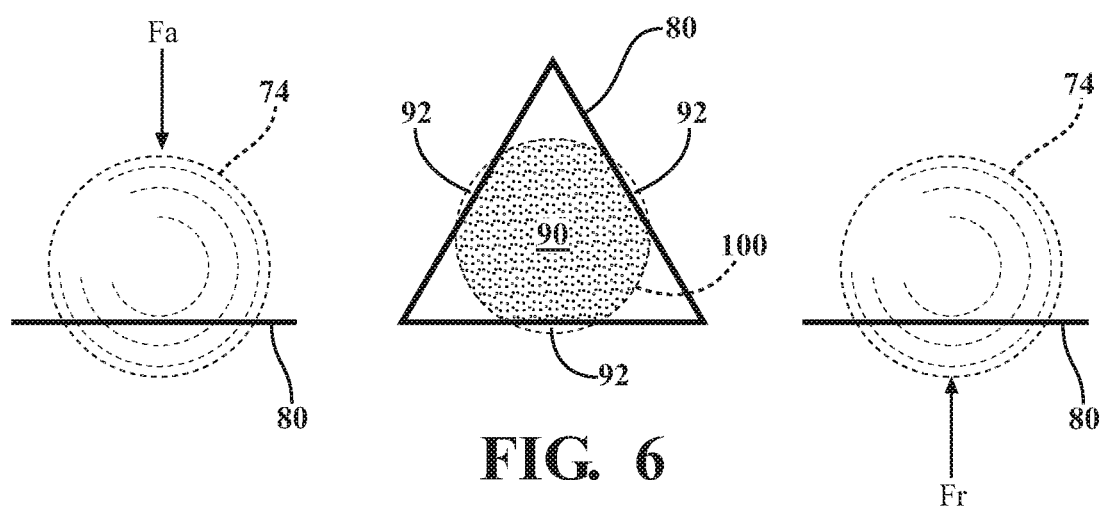
FIG. 6 illustrates another example of using the penetration factor based on projected area to generate a reactive force responsive to interaction of the virtual volume with one polygonal element of the virtual boundary.
Figure 7:
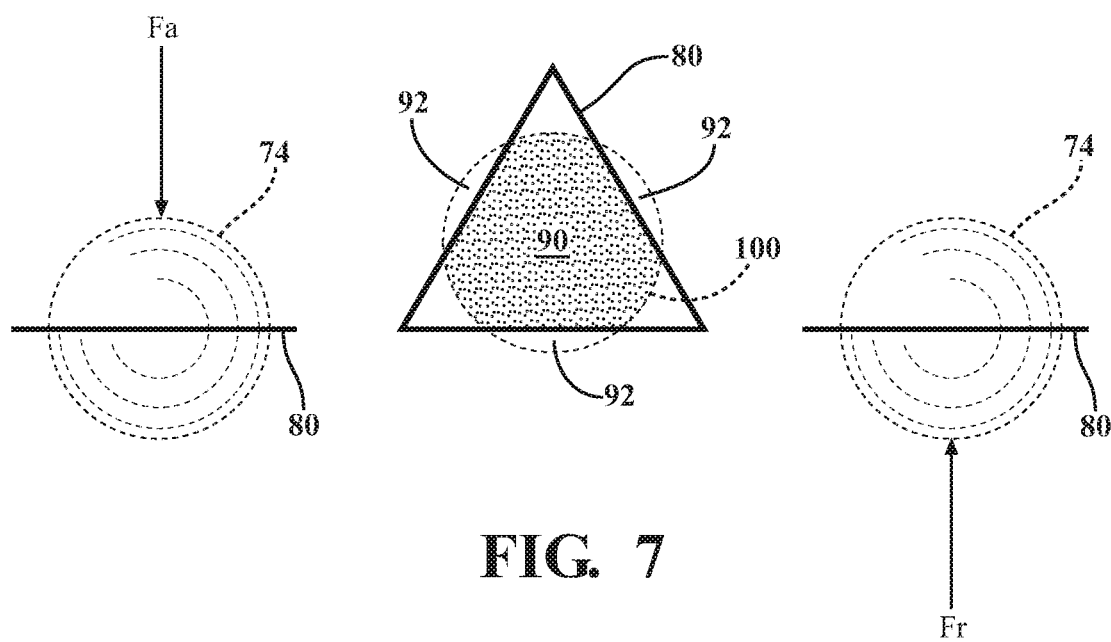
FIG. 7 illustrates yet another example of using the penetration factor based on projected area to generate a reactive force responsive to interaction of the virtual volume with one polygonal element of the virtual boundary.

Referring now to FIGS. 5-7, examples are shown illustrating the projected area 90 in a situation where the virtual volume 74 (e.g., a sphere) penetrates one polygonal element 80 (e.g., a triangle) in accordance with the impact force ($F_a$). For simplicity in illustration, a convention is used in the Figures wherein a length of a force arrow is representative of a magnitude of the force. Thus, greater magnitudes of the force are represented by longer arrows and lesser the magnitudes of the force are represented by shorter arrows. It is to be appreciated that arrow lengths are illustrative and are not intended to represent direct mathematical correlation between the projected area 90 and the corresponding reactive force (Fr).

It should be understood that for simplicity, the figures illustrate three separate examples and do not represent gradual penetration of the virtual boundary 55 by the virtual volume 74 over time. Mainly, for each example, the respective reactive force (Fr) is shown to offset the respective impact force ($F_a$) fully, thereby eliminating penetration by the virtual boundary 55.

Of course, gradual penetration by the virtual volume 74 is likely to occur and one skilled in the art should appreciate that the techniques are fully capable of iteratively applying the reactive force (Fr) to the virtual volume 74 for various iterations of impact force ($F_a$). For subsequent changes of state of the tool 20 relative to the virtual boundary 55, the controller 30 is configured to iteratively compute the reactive force (Fr), iteratively apply the reactive force (Fr), and iteratively command the manipulator 14 to move the tool 20 in accordance with application of the reactive force (Fr) to the virtual volume 74 in the virtual simulation 72. For instance, the reactive force (Fr) may only partially displace the virtual volume 74 relative to the virtual boundary 55 such that the virtual volume 74 continues to intersect the virtual boundary 55. In such situations, the subsequent state of the tool 20 after such partial displacement is tracked and the virtual volume 74 pose is updated in the virtual simulation 72. The update pose of the virtual volume 74 may cause a different (e.g., lesser) intersection with the virtual boundary 55, and hence, a lesser projected area 50 and ultimately, a subsequent reactive force (Fr) of lesser magnitude. In turn, the tool 20 may be partially displaced further from the virtual boundary 55. This process may be repeated iteratively until penetration by the virtual boundary 55 is completely rescinded or until a threshold is reached.

For the specific examples, the polygonal element 80 is shown below the virtual volume 74 and hence terms of orientation (such as upper or lower) may be used to describe this orientation. Such terms of orientation are described relative to the subject examples and are not intended to limit the scope of the subject matter. It is to be appreciated that other orientations are possible, such as the virtual volume 74 approaching the polygonal element 80 from below or from the side.

Additionally, the projected area 90 in FIGS. 5-7 is based on a circle because the virtual volume 74 in these examples is a sphere. Of course, depending on the configuration, shape, and/or pose of the virtual volume 74, the intersection, and hence, the projected area 90 may be a size or shape other than shown in the Figures. Furthermore, the projected area 90 in FIGS. 5-7 is shown in the center of the polygonal element 80 for simplicity, and based on the assumption that the virtual volume 74 has penetrated the geometrical center of the area of the polygonal element 80. However, depending on the configuration, shape, and/or pose of the virtual volume 74, the projected area 90 may be offset from the center of the polygonal element 80.

Referring now to FIG. 5, the left-most illustration shows a side view of the virtual volume 74 and polygonal element 80. In accordance with the impact force ($F_a$), the lower-most tip of the virtual volume 74 slightly penetrates the polygonal element 80. The projected area 90 (shown in the middle figure of FIG. 5) represents the intersection of the virtual volume 74 and the polygonal element 80, and is a circle. A cross-section 100 of the virtual volume 74 at the plane of intersection coincides with the projected area 90 in this example. The projected area 90 in FIG. 5 is small relative to the area of the polygonal element 80 because only the lower-most tip of the virtual volume 74 is penetrating. In the right-most illustration in FIG. 5, the reactive force (Fr) computed based on the projected area 90 is shown. The reactive force (Fr) is shown with an arrow applied to the virtual volume 74 in a direction normal to the plane of the polygonal element 80 and opposing the impact force ($F_a$). In FIG. 5, the arrow for the reactive force (Fr) is sized to reflect the relative projected area 90.

In FIG. 6, the virtual volume 74 more deeply penetrates the polygonal element 80, and hence, a greater intersection between the virtual volume 74 and the polygonal element 80 exists. Thus, the projected area 90 in FIG. 6 (middle illustration) is greater than the projected area 90 in FIG. 5. The projected area 90 in FIG. 6 is based on a circle (i.e., from the intersection of the sphere), but is not circular. Instead, the projected area 90 is bound by the perimeter of the polygonal element 80 and therefore, is considered in as much as the projected area 90 is bound within the perimeter of the polygonal element 80. The cross-sectional area 100 of the virtual volume 74 at the plane of intersection extends beyond the bounds of the polygonal element 80, and as such, unbound regions exist at 92 in FIG. 6. These unbound regions 92 are not considered in the computation of the reactive force (Fr) for the impacted polygonal element 80. In the right-most illustration in FIG. 6, the computed reactive force (Fr) is shown having an arrow sized greater than the arrow for the reactive force (Fr) in FIG. 5 because the projected area 90 in FIG. 6 is greater than the projected area 90 in FIG. 5.

In FIG. 7, an even greater penetration of the polygonal element 80 by the virtual volume 74 is shown. Specifically, one-half of the spherical virtual volume 74 penetrates the polygonal element 80. As expected, the projected area 90 in FIG. 7 (middle illustration) is greater than the projected area 90 in FIG. 6. Once again, unbound regions 92 are present and are disregarded in the computation of the reactive force (Fr). As expected with deeper penetration, the area of the unbound regions 92 is also greater than the area of the unbound regions 92 in FIG. 6. In the right-most illustration in FIG. 7, the computed reactive force (Fr) is shown having an arrow sized greater than the arrow for the reactive force (Fr) in FIG. 6. Those skilled in the art appreciate that measures may be taken to account for situations where penetration is so deep that the projected area 90 actually decreases because of the shape of the virtual volume 74. For instance, this may occur in FIG. 7 when more than one-half of the spherical virtual volume 74 penetrates the polygonal element 80. Such measures may include computing and combing more than one projected area 90 for any given penetration for any single polygonal element 80 and/or taking into account the displaced volume of the virtual boundary 55.

As should be apparent based on FIGS. 5-7, the projected area 90 varies with respect to the linear depth of penetration. However, the projected area 90 does not change linearly with respect to linear depth of penetration because the penetrating body is volumetric and does not apply a linear impact force (Fa) to the polygonal element 80 and/or virtual boundary 55. Instead, the penetrating body applies a higher order impact force (Fa) as a function of the volumetric shape of the virtual volume 74. Accordingly, the projected area 90 changes with respect to linear depth of penetration according to this higher order volumetric function. Said differently, the projected area 90 accounts for the displaced volume or penetrating volume of the virtual volume 74.

This variable response occurs in part because the virtual volume 74 in the examples shown has only one face (e.g., is spherical) and does not have identical cross-sectional areas adjacent to one another. For instance, the projected area 90 would have been identical for FIGS. 5-7 had the virtual volume 74 been a cube having a lower face penetrating the polygonal element 80 (with flat sides coinciding). Hence, the reactive forces (Fr) for each example would have been the same despite the relative differences in linear depth of penetration warranting different reactive forces (Fr) according to the techniques described herein.

Thus, reactive forces (Fr) computed in response to penetration by the virtual volume 74 are variably responsive to the linear depth of penetration. However, even though the reactive force (Fr) may change with changes in the linear depth of penetration, the reactive force (Fr) is indeed computed based on the projected area 90. The reactive force (Fr) is not computed simply based on the linear depth by which the virtual volume 74 protrudes into the polygonal element 80 and/or virtual boundary 55.

Figure 8:
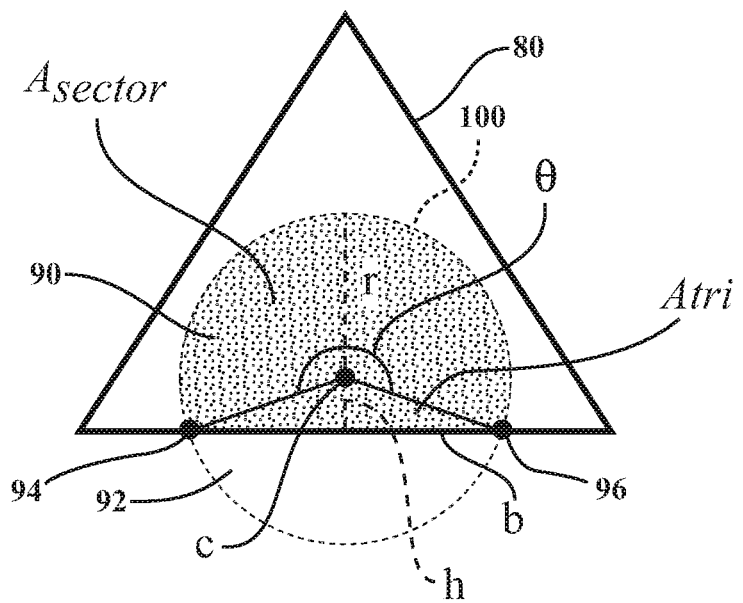
FIG. 8 illustrates one example of computing projected area with respect to one polygonal element of the virtual boundary.
Figure 9:
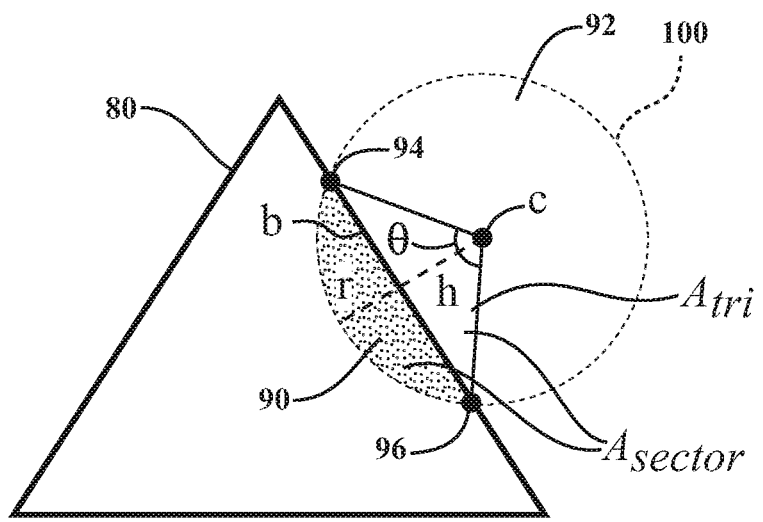
FIG. 9 illustrates another example of computing projected area with respect to one polygonal element of the virtual boundary.

Examples of techniques for computing the projected area 90 are shown in FIGS. 8 and 9. As described, the projected area 90 for a given polygonal element 80 is illustrated by the shaded region within the polygonal element 80 and excludes any unbound regions 92 extending beyond the polygonal element 80. In FIG. 8, calculations of the projected area 90 specifically for a triangular polygonal element 80 are shown.

In FIG. 8, the projected area 90 is derived from intersection with a spherical virtual volume 74 and thus is circular-based. A circle is shown in FIG. 8 and represents the cross-sectional area 100 of the virtual volume 74 at the plane of intersection with the triangular polygonal element 80. The circle is off-center from the geometrical center of the triangular polygonal element 80 and intersects a lower edge of the polygonal element 80 at intersection points 94 and 96. In turn, the cross-sectional area 100 is cut-off by the lower edge, resulting in the unbound region 92, as shown. Center point (c) is the center of the cross-sectional area 100 of the virtual volume 74 and radius (r) is the radius of the cross-sectional area 100.

In this example, the projected area 90 is computed by determining an overlap between the circle and the polygonal element 80. Specifically, in this situation, wherein intersection of the circle occurs with respect to only one edge (and no vertices) of the triangular polygonal element 80, the projected area 90 is computed by breaking down the overlap into a triangular area $A_{tri}$ and a circular sector area $A_{sector}$. The triangular area $A_{tri}$ is defined within three points, i.e., center point (c), and intersection points 94, 96. A base (b) of the triangular area $A_{tri}$ is defined between the intersection points 94, 96 and a height (h) of the triangular area $A_{tri}$ is defined between center point (c) and the base (b). The triangular area $A_{tri}$ is computed using the equation $A_{tri}=\frac{1}{2}bh$. The circular sector area $A_{sector}$ is based on the sector angle (θ), which is defined about the center point (c) and between two legs of the triangular area $A_{tri}$ defined respectively between the center point (c) and each intersection point 92, 94. The circular sector area $A_{sector}$ is computed using the equation $A_{sector}=\pi r^2*\theta/360$ (degrees). Notably, in this example, the center point (c) of the circle is located within the polygonal element 80. Hence, the circular sector area $A_{sector}$ is also located within the polygonal element 80. With the triangular area $A_{tri}$ and the circular sector area $A_{sector}$ occupying the entire shaded region, as shown in FIG. 8, the projected area $A_{proj}$ is computed by adding $A_{tri}$ and $A_{sector}$.

FIG. 9 is yet another example illustrating computation of the projected area $A_{proj}$ based on triangular polygonal element 80 and the circular cross-section 100 of the virtual volume 74. In this situation, intersection of the circular cross-section 100 once again occurs with respect to only one edge (and no vertices) of the triangular polygonal element 80. However, in this example, the center point (c) of the circular cross-section 100 is located outside of the polygonal element 80. As a result, the entire triangular area $A_{tri}$ and a portion of the circular sector area $A_{sector}$ are also located outside the polygonal element 80. Thus, unlike the projected area 90 of FIG. 8, which was computed by adding together the triangular area $A_{tri}$ and the circular sector area $A_{sector}$, the projected area 90 of FIG. 9 is computed by subtracting the triangular area $A_{tri}$ from the circular sector area $A_{sector}$. The projected area 90 of FIG. 9 is lesser than the projected area 90 of FIG. 8.

It should be reiterated that the calculations with respect to FIGS. 8 and 9 are specific not only to a triangular polygonal element 80 and a circular cross-section 100 of the virtual volume 74, but further specific to intersection of the circle with respect to only one edge of the triangular polygonal element 80 and no vertices of the triangular polygonal element 80. Of course, the projected area 90 and hence the calculations for computing the projected area 90 may be different depending on the geometry of the polygonal element 80, the geometry of the virtual volume 74, and the relative locations of these geometries to each other. Furthermore, for the examples shown, computations of the projected area 90 will differ depending on how many edges (from 0 up to 3) and vertices (from 0 up to 3) of the triangular polygonal element 80 are intersected by the circular cross-section 100 of the virtual volume 74. Geometric computation of the projected area 90 is contemplated for any geometric configuration and situation other than those described herein.

Figure 10:
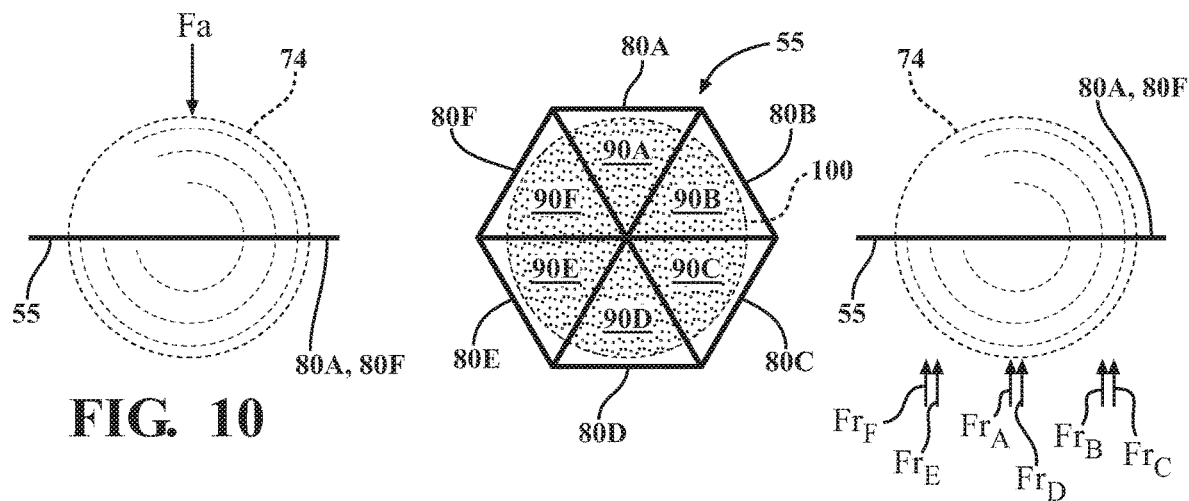
FIG. 10 illustrates one example of using projected areas to generate multiple reactive forces responsive to interaction of the virtual volume with multiple polygonal elements of the virtual boundary.
Figure 11:
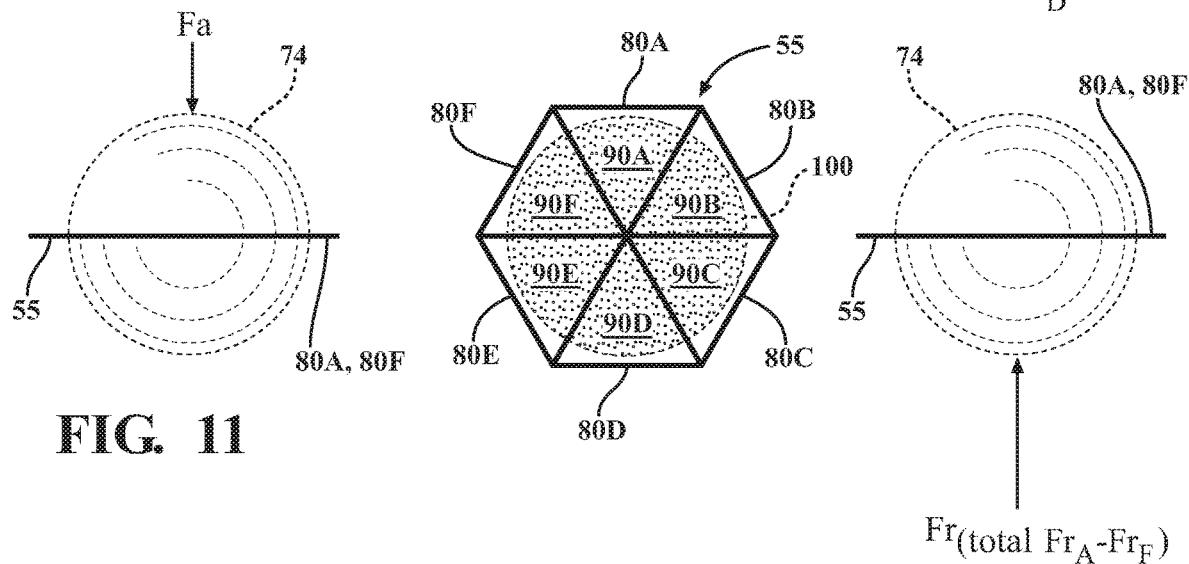
FIG. 11 illustrates one example of using projected areas to generate a combined reactive force responsive to interaction of the virtual volume with multiple polygonal elements of the virtual boundary.
Figure 12:
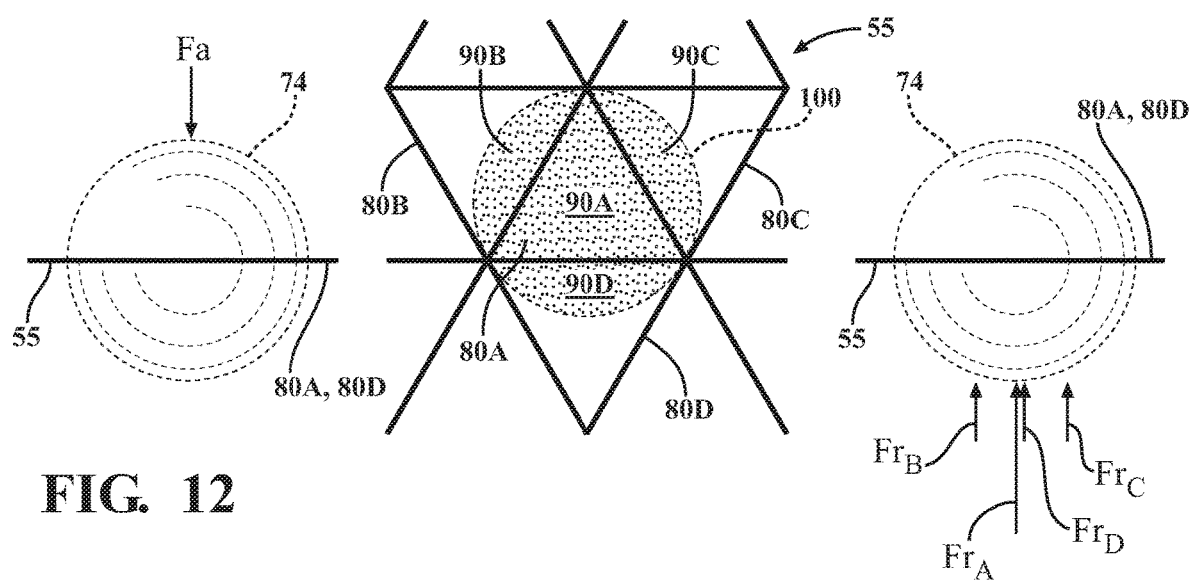
FIG. 12 illustrates another example of using projected areas to generate multiple reactive forces responsive to interaction of the virtual volume with multiple polygonal elements of the virtual boundary.

Referring to FIGS. 10-12, examples are shown wherein multiple reactive forces (e.g., $Fr_A$-$Fr_F$) are generated in response to simultaneous penetration of multiple polygonal elements (e.g., 80A-80F) by the virtual volume 74 in the virtual simulation 72. For simplicity, the examples in FIGS. 10-12 continue to reference triangular polygonal elements 80 and a circular cross-section 100 of the virtual volume 74.

In FIG. 10, the spherical virtual volume 74 penetrates the virtual boundary 55 comprised of polygonal elements 80A-80F, which for this example are assumed to be on the same plane. Of course, the mesh of the virtual boundary 55 may comprise more polygonal elements other than polygonal elements 80A-80F and the various polygonal elements 80 may be adjacently disposed next to each other at angles such that they are non-planar. Unlike FIGS. 5-9, wherein intersection with only one polygonal element 80 was shown and described, in FIG. 10, the circular cross-section 100 of the virtual volume 74 intersects each of the polygonal elements 80A-80F at a center vertex shared among polygonal elements 80A-80F. Thus, the projected areas 90A-90F mapped onto each respective polygonal element 80A-80F are identical. Identical projected areas 90A-90F are described for simplicity in this example, and it should be understood that a different shape (or absence) of the projected area 90 for each polygonal element 80A-80F is possible. Reactive forces ($Fr_A$-$Fr_F$) are computed for respective polygonal elements 80A-80F. Each reactive force ($Fr_A$-$Fr_F$) is related to the respective projected area 90A-90F defined by intersection of the virtual volume 74 with each polygonal element 80A-80F. Again, each projected area 90A-90F is bound by each polygonal element 80A-80F. Thus, in this example, the reactive forces ($Fr_A$-$Fr_F$) are also identical.

In FIG. 10, the controller 30 is configured to apply the multiple reactive forces ($Fr_A$-$Fr_F$) simultaneously to the virtual volume 74 to offset penetration of the virtual boundary 55 by the virtual volume 74. In the specific example of FIG. 10, each of the multiple reactive forces ($Fr_A$-$Fr_F$) is applied individually to the virtual volume 74. For instance, each polygonal element 80 may individually react to penetration by the virtual volume 74. The reactive forces ($Fr_A$-$Fr_F$) are applied according to positions corresponding to the respective polygonal element 80A-80F, and hence, may differ slightly from the positions shown in FIG. 10, which are limited by the side-view.

The situation in FIG. 11 is similar to the situation in FIG. 10 except that the controller 30 combines the multiple reactive forces ($Fr_A$-$Fr_F$) to generate a combined reactive force ($Fr_{Total}$). The controller 30 is configured to apply the single combined reactive force ($Fr_{Total}$), at one time, to the virtual volume 74 to offset penetration of the virtual boundary 55 by the virtual volume 74. A magnitude of the combined reactive force ($Fr_{Total}$) may be computed by summing respective magnitudes of the multiple reactive forces ($Fr_A$-$Fr_F$). In this case, the magnitude of the combined reactive force ($Fr_{Total}$) is six times the respective magnitude of any one of the reactive forces ($Fr_A$-$Fr_F$). Location of the combined reactive force ($Fr_{Total}$) may be computed by averaging or finding a center of the respective locations of the multiple reactive forces ($Fr_A$-$Fr_F$). In this case, the location of the combined reactive force ($Fr_{Total}$) is at the center vertex shared among polygonal elements 80A-80F. Since the assumption in this example is that the polygonal elements 80A-80F are located in the same plane, the direction of the combined reactive force ($Fr_{Total}$) is normal to the plane and opposing the impact force (Fa). The magnitude, location, and direction of the combined reactive force ($Fr_{Total}$) may be computed according to methods other than those described herein.

In some examples, the controller 30 can apply a weighting factor to each of the reactive forces (Fr) such that the combined reactive force is constant for any given simultaneous penetration of multiple polygonal elements 80 by the virtual volume 74. In other words, the controller 30 can utilize affine combination algorithms to manipulate the weighting factors such that the sum of these weighting factors is constant. For example, weighting factors may be defined to sum to one when the virtual boundary 55 is a flat surface. The weighting factors may be defined to sum to a number greater than one when two virtual boundaries 55 are close to perpendicular or perpendicular. The weighting factors may be defined to sum to a number less than one at an edge of the virtual boundary. This technique helps to provide a predictable and smooth reactive response to penetration of the virtual volume 55 for these given scenarios such that the user is provided with a natural reactive response. In other words, the user does not experience unexpected increases or decreases in force.

In FIG. 12, the spherical virtual volume 74 penetrates the virtual boundary 55 comprised of polygonal elements 80A-80D. Unlike FIGS. 10 and 11, the circular cross-section 100 of the virtual volume 74 in FIG. 12 does not equally intersect each of the polygonal elements 80A-80D. Instead, the projected area 90A mapped onto polygonal element 80A is greater than the projected areas 90B-90D mapped onto polygonal elements 80B-80D. Projected areas 90B-90D are identical. Reactive forces ($Fr_A$-$Fr_F$) are computed for each polygonal element 80A-80F. The reactive force ($Fr_A$) related to projected area 90A is greater than each of the reactive forces ($Fr_B$-$Fr_D$) related to projected areas 90B-90D because projected area 90A is greater than projected areas 90B-90D. Again, the reactive forces ($Fr_A$-$Fr_D$) are applied according to positions corresponding to the respective polygonal element 80A-80D, and hence, may differ slightly from the positions shown in FIG. 12, which are limited by the side-view.

FIG. 12 further exemplifies the dynamic response of the projected area techniques described herein because the linear depth of penetration is the same for each of the polygonal elements 80A-80D. However, since the projected area 90A for polygonal element 80A is greater than the respective projected areas 90B-90D for polygonal elements 80B-80D, the reactive force ($Fr_A$) related to projected area 90A is greater than each of the other reactive forces ($Fr_B$-$Fr_D$) and accurately accounts for the penetration impact provided by this specific virtual volume 74. Thus, this example reiterates that the projected area 90, and consequently, the reactive force (Fr) do not change linearly with respect to linear depth of penetration.

Figure 13:
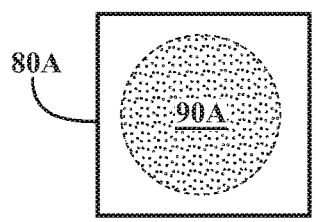
FIG. 13 illustrates one example of using projected areas to generate reactive forces responsive to interaction of the virtual volume with polygonal elements forming an outside corner of the virtual boundary.
Figure 14:
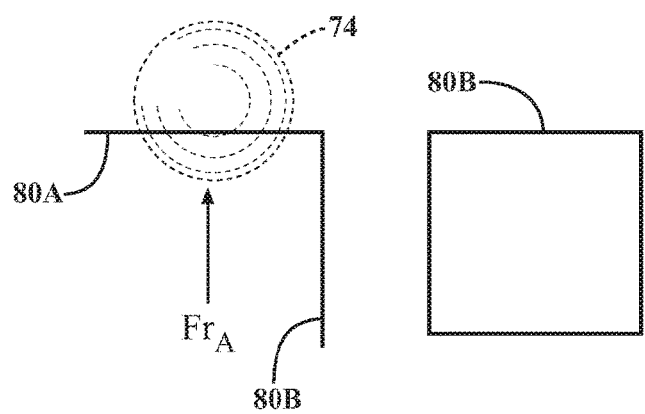
FIG. 14 illustrates another example of using projected areas to generate reactive forces responsive to interaction of the virtual volume with polygonal elements forming the outside corner of the virtual boundary.
Figure 15:
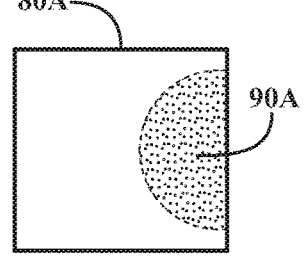
FIG. 15 illustrates yet another example of using projected areas to generate reactive forces responsive to interaction of the virtual volume with polygonal elements forming the outside corner of the virtual boundary.
Figure 15:
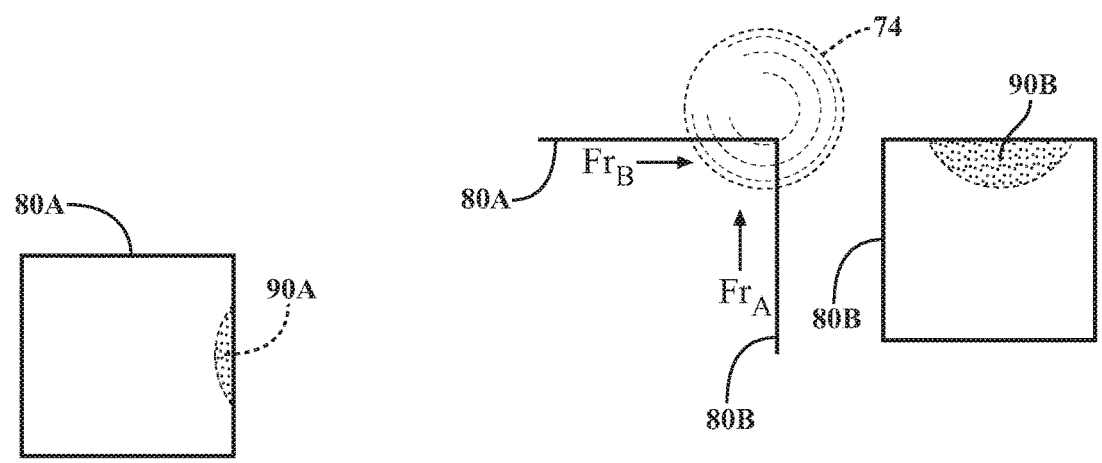
Figure 15:
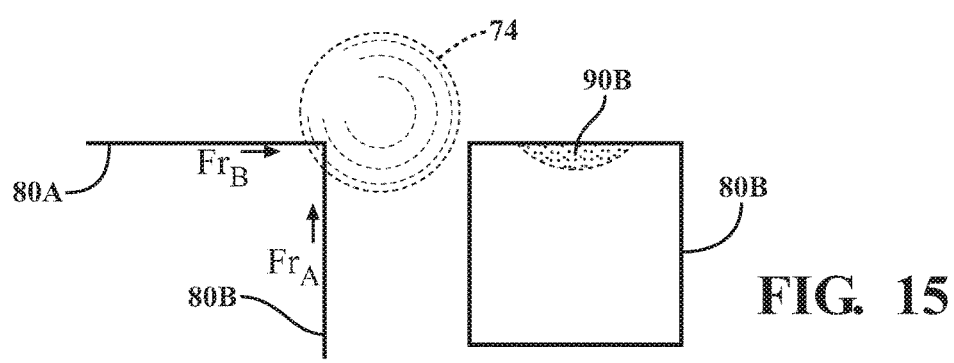

The previous examples have described situations in which the polygonal elements 80 are located in the same plane. The techniques described herein are equally applicable to situations wherein the polygonal elements 80 are located in different planes. One example of this situation is where the virtual volume 74 encounters a corner defined by the polygonal elements 80. For example, FIGS. 13-15 illustrate use of the projected area 90 in a situation where the virtual volume 74 (e.g., a sphere) penetrates two polygonal elements 80A, 80B, (e.g., squares) in accordance with the impact force ($F_a$). Specifically, the two polygonal elements 80A, 80B form an outside corner of the virtual boundary 55.

It should be understood that for simplicity FIGS. 13-15, as shown, illustrate three separate examples and do not represent gradual penetration of the virtual boundary 55 by the virtual volume 74 over time. Mainly, for each example, the respective reactive force (Fr) is shown to offset the respective impact force ($F_a$) fully, thereby eliminating penetration by the virtual boundary 55. Of course, gradual penetration by the virtual volume 74 is likely to occur and one skilled in the art should appreciate that the techniques are fully capable of iteratively applying the reactive force (Fr) to the virtual volume 74 for various iterations of impact force ($F_a$).

Referring now to FIG. 13, a side view of the virtual volume 74 and polygonal elements 80A, 80B are shown. Further shown in FIG. 13 are a respective top view of polygonal element 80A and a respective front view of polygonal element 80B. The virtual volume 74 penetrates polygonal element 80A but not polygonal element 80B. The projected area 90A is a circle and represents the intersection of the virtual volume 74 and the polygonal element 80A. The reactive force ($Fr_A$) is computed based on the projected area 90A and is applied to the virtual volume 74 in a direction opposing the impact force ($F_a$). In this example, the projected area 90A is mapped to a square center of polygonal element 80A because of the location of penetration by the virtual volume 74. Thus, the reactive force ($Fr_A$) is applied to a location that is central to the polygonal element 80A, and hence, central to the penetrating virtual volume 74. Furthermore, the projected area 90A is a full cross-sectional area 100 of the virtual volume 74. Accordingly, the reactive force ($Fr_A$) is applied with a relatively large magnitude.

In the example of FIG. 14, the virtual volume 74 is shown to penetrate both polygonal elements 80A, 80B at the outside corner. Due to the location of penetration, the respective projected areas 90A, 90B mapped to polygonal elements 80A, 80B are each only a portion of the cross-sectional area 100 of the virtual volume 74. The reactive force ($Fr_A$) computed based on projected area 90A is applied to the virtual volume 74 in a direction opposing the impact to polygonal element 80A. The reactive force ($Fr_B$) computed based on projected area 90B is applied to the virtual volume 74 in a different direction, i.e., opposing the impact to polygonal element 80B. Based on the location of impact, projected area 90A is mapped to a right edge of polygonal element 80A and projected area 90B is mapped to an upper edge of polygonal element 80B. Thus, reactive force ($Fr_A$) is applied to a location that is near the right edge of polygonal element 80A and reactive force ($Fr_B$) is applied to a location that is near the upper edge of polygonal element 80B. Furthermore, since the projected areas 90A, 90B are each only a portion of the cross-sectional area 100 of the virtual volume 74, the reactive forces ($Fr_A$), ($Fr_B$) are applied with corresponding magnitudes, each of which are less than the magnitude of reactive force ($Fr_A$) applied in FIG. 13. This is so despite that fact that the linear depth of penetration is the same between FIGS. 13 and 14.

In FIG. 15, an even lesser portion of the virtual volume 74 penetrates both polygonal elements 80A, 80B at the outside corner, as compared with FIG. 14. The linear depth of penetration is also less than that of FIGS. 13 and 14. As compared with FIG. 14, the projected areas 90A, 90B in FIG. 15 are lesser and the reactive force ($Fr_A$) is applied nearer the right edge of polygonal element 80A and reactive force ($Fr_B$) is applied nearer the upper edge of polygonal element 80B. Furthermore, the reactive forces ($Fr_A$), ($Fr_B$) are applied with corresponding magnitudes that are lesser than the magnitude of reactive forces ($Fr_A$), ($Fr_B$) applied in FIG. 14.

As should be apparent from these examples, the techniques for using projected area 90 to compute the reactive forces ($Fr_A$), ($Fr_B$) at the outside corner provide a natural response to opposing the virtual boundary 55. For example, even though the one polygonal element 80A is penetrated in FIG. 13, and two polygonal elements 80A, 80B are penetrated at the outside corner in FIG. 14, the techniques provide gradual increase in reactive force (Fr). In other words, increasing projected area 90 translates into increasing reactive force (Fr) and decreasing projected area 90 translates into decreasing reactive force (Fr). In so doing, the techniques avoid discrete jumps in reactive force (Fr) that move the tool 20 abruptly or unnaturally during encounters with the virtual boundary 55. The projected area 90A in FIG. 13 is roughly the same area as the combination of the projected areas 90A, 90B in FIG. 14, thereby providing a smooth reactive response even though penetration by the virtual volume 74 has effectively doubled at the given linear depth. In other words, by using the projected areas 90A, 90 to compute the reactive forces ($Fr_A$), ($Fr_B$), respectively, unexpected kick back of the tool 20 while rolling over the outside corner is mitigated. Thus, the techniques described herein solve surface modeling issues relating to corners. The techniques apply fully to any other examples wherein multiple non-planar polygonal elements 80 are simultaneously penetrated by the virtual volume 74. Examples include, but are not limited to, inside corners, peaks, valleys, etc.

B. Projected Arc

Figure 16:
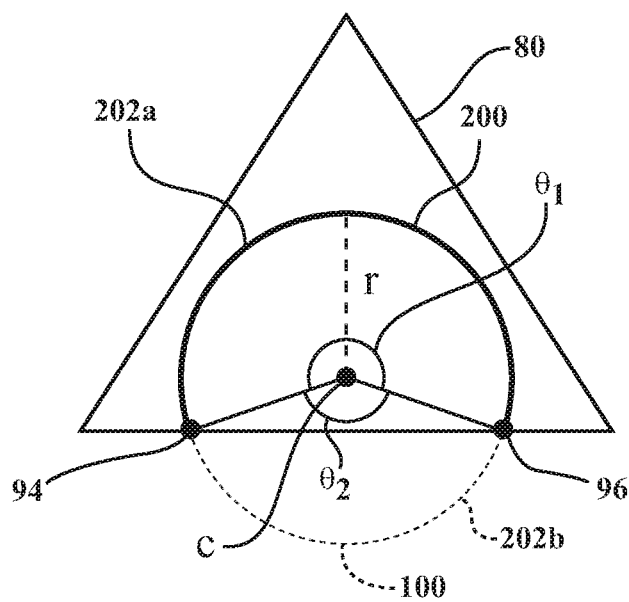
FIG. 16 illustrates one example of computing the penetration factor based on projected arc with respect to one polygonal element of the virtual boundary.
Figure 17:
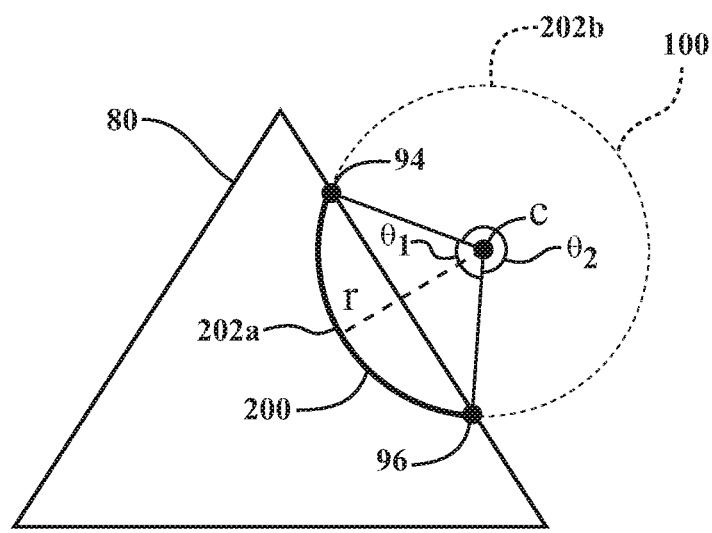
FIG. 17 illustrates another example of computing the penetration factor based on projected arc with respect to one polygonal element of the virtual boundary.

In accordance with another example, as shown in FIGS. 16 and 17, the controller 30 is configured to compute the reactive force (Fr) based on the penetration factor being related to a projected arc 200. The projected arc 200 is defined by a combination of any arcs 202 of the cross-sectional area 100 of the virtual volume 74 being bound by the geometry of the polygonal element 80 during intersection of the virtual volume 74 with the polygonal element 80.

Here, the term "projected" is a mathematical expression indicating that the arcs 202 defined by intersection of the virtual volume 74 with the polygonal element 80 are mapped relative to the planar surface of the polygonal element 80.

The projected arc 200 is bound by the polygonal element 80. Specifically, the projected arc 200 is bound by a perimeter of the polygonal element 80. In other words, the projected arc 200 for a single polygonal element 80 is considered in as much as the projected arc 200 exists within the perimeter of the polygonal element 80.

The virtual volume 74 is defined such that the projected arc 200 changes non-linearly relative to a linear depth of penetration (i.e., the distance by which the virtual volume 74 protrudes into the polygonal element 80 and/or virtual boundary 55) by the virtual volume 74. Although the reactive force (Fr) may change with changes in the linear depth of penetration, the reactive force (Fr) is computed based on the projected arc 200 and without computationally accounting for the linear depth of penetration.

In this example, the reactive force (Fr) is related to the projected arc 200. In one example, the reactive force (Fr) is directly correlated with the projected arc 200. Additionally or alternatively, the reactive force (Fr) is proportional to the projected arc 200.

The reactive force (Fr) may be applied as a vector being normal to the plane of the polygonal element 80. The location of the vector with respect to the plane of the polygonal element 80 may vary depending on the location of projected arc 200 mapped on to the polygonal element 80. The magnitude of the reactive force (Fr) may vary depending on the size of the projected arc 200. The reactive force (Fr) vector may be at an angle that is not normal with respect to the plane of the polygonal element 80 depending on the projected arc 200 and/or the pose of the virtual volume 74 during penetration. Techniques for computing the reactive force (Fr) from the projected arc 200 are described below.

For comparative purposes, the same geometrical examples of FIGS. 8 and 9, used above to describe computation of the projected area 90 are used in FIGS. 16 and 17 to describe computation of the projected arc 200.

In FIG. 16, the cross-sectional area 100 of the virtual volume 74 at the plane of intersection with the triangular polygonal element 80 is shown. The circle is off-center from the geometrical center of the triangular polygonal element 80 and intersects a lower edge of the polygonal element 80 at intersection points 94 and 96. In turn, the cross-sectional area 100 is cut-off by the lower edge. Center point (c) is the center of the cross-sectional area 100 of the virtual volume 74 and radius (r) is the radius of the cross-sectional area 100.

In this example, the projected arc 200 is defined by a combination of any arcs 202 of the cross-sectional area 100 of the virtual volume 74 being bound by the geometry of the polygonal element 80 during intersection of the virtual volume 74 with the polygonal element 80. In other words, the projected arc 200 is computed by determining any arcs 202 of perimeter of the cross-sectional area 100 that lie within the area of the polygonal element 80. Specifically, in this situation, wherein intersection of the circle occurs with respect to only one edge (and no vertices) of the triangular polygonal element 80, the projected arc 200 is computed by breaking down cross-sectional area 100 into arc segments 202a, 202b defined respectively by sector angles $\theta_1$ and $\theta_2$. Notably, in this example, the center point (c) of the cross-sectional area 100 is located within the polygonal element 80. The sector angles $\theta_1$ and $\theta_2$ are each defined about the center point (c) between intersection points 94, 96 and equal 360 degrees when combined. As shown, arc segment 202a based on sector angle $\theta_1$ lies entirely within and is bound by the polygonal element 80, while arc segment 202b based on sector angle $\theta_2$ lies entirely outside of and is unbound by the polygonal element 80. The projected arc can be computed using the following equation $Arc_{proj} = \theta_n/360$, where the angle $\theta_n$ is a sector angle creating an arc segment 202 that is bound by the polygonal element 80. In the example of FIG. 16, $Arc_{proj} = \theta_1/360$ because $\theta_1$ creates an arc segment 202a that is bound by the polygonal element 80. There may be more than one sector angle in the numerator of this equation, i.e., $Arc_{proj} = (\theta_n + \theta_m + \ldots)/360$, and these sector angles may be added together to establish the projected arc 200. The resultant value of this equation may be multiplied, scaled, or otherwise modified to standardize the projected arc 200 effect. For example, the projected arc 200 may alternatively be based on a length of the arc segment 202 rather than the degrees of its respective sector angle.

FIG. 17 is yet another example illustrating computation of the projected arc 200 based on triangular polygonal element 80 and the circular cross-section 100 of the virtual volume 74. In this situation, intersection of the circular cross-section 100 once again occurs with respect to only one edge (and no vertices) of the triangular polygonal element 80. However, in this example, the center point (c) of the circular cross-section 100 is located outside of the polygonal element 80. The projected arc 200 is computed in a similar fashion. However, sector angle $\theta_1$ has decreased as compared with FIG. 16 and sector angle $\theta_2$ has increased in comparison to FIG. 16. Arc segment 202a, created from sector angle $\theta_1$ has reduced in length in comparison to FIG. 16 and arc segment 202b, created from sector angle $\theta_2$ has increased in length in comparison to FIG. 16. The projected arc 200 is based on arc segment 202a, which is bound within the polygonal element 80. Therefore, comparing FIGS. 16 and 17, this example illustrates how a lesser penetrative impact by the virtual volume 74 results in a lesser projected arc 200, and generally, a lesser reactive force (Fr).

It should be reiterated that the calculations with respect to FIGS. 16 and 17 are specific not only to a triangular polygonal element 80 and a circular cross-section 100 of the virtual volume 74, but further specific to intersection of the circle with respect to only one edge of the triangular polygonal element 80 and no vertices of the triangular polygonal element 80. Of course, the projected arc 200 and hence the calculations for computing the projected arc 200 may be different depending on the geometry of the polygonal element 80, the geometry of the virtual volume 74, and the relative locations of these geometries to each other. Furthermore, for the examples shown, computations of the projected arc 200 will differ depending on how many edges (from 0 up to 3) and vertices (from 0 up to 3) of the triangular polygonal element 80 are intersected by the circular cross-section 100 of the virtual volume 74. More complex arc segments 202 can be computed in instances where the cross-sectional area 100 of the virtual volume 74 is not circular, but rather elliptical or the like. Geometric computation of the projected arc 200 is contemplated for any geometric configuration and situation other than those described herein.

As should be apparent based on FIGS. 16 and 17, the projected arc 200 varies with respect to the linear depth of penetration. However, the projected arc 200 does not change linearly with respect to linear depth of penetration because the penetrating body is volumetric and does not apply a linear impact force (Fa) to the polygonal element 80 and/or virtual boundary 55. Instead, the penetrating body applies a higher order impact force (Fa) as a function of the volumetric shape of the virtual volume 74. Accordingly, the projected arc 200 changes with respect to linear depth of penetration according to this higher order volumetric function. Said differently, the projected arc 200 accounts for the displaced volume or penetrating volume of the virtual volume 74 by capturing the arc segments 202 that are within the plane of the polygonal element 202. Once again, the variable nature of the projected arc 200 occurs in part because the virtual volume 74 in the examples shown in FIGS. 16 and 17 has only one face (e.g., is spherical) and does not have identical cross-sectional areas adjacent to one another.

Thus, reactive forces (Fr) computed in response to penetration by the virtual volume 74 are variably responsive to the linear depth of penetration. However, even though the reactive force (Fr) may change with changes in the linear depth of penetration, the reactive force (Fr) is indeed computed based on the projected arc 200 in these examples. The reactive force (Fr) is not computed simply using the linear depth by which the virtual volume 74 protrudes into the polygonal element 80 and/or virtual boundary 55.

The examples and different possibilities described with respect to FIGS. 5-7 shown for projected area 90 may be fully understood with respect to projected arc 200 and therefore are not repeated for simplicity. Of course, one skilled in the art would appreciate that reactive forces (Fr) computed based on projected arc 200 are likely to be different as compared with those reactive forces (Fr) shown computed based on projected area 90. Furthermore, iterative application of reactive force (Fr) computed based on recalculation of projected arc 200 is fully contemplated.

Furthermore, the examples of FIGS. 10-12 showing multiple reactive forces (e.g., $Fr_A$-$Fr_F$) computed using projected area 90 and generated in response to simultaneous penetration of multiple polygonal elements (e.g., 80A-80F) by the virtual volume 74 may be fully understood with respect to the techniques described herein using projected arc 200. Mainly, each reactive force ($Fr_A$-$Fr_F$) would be related to the respective projected arc 200 bound by each polygonal element 80A-80F. For projected arc 200, the reactive forces (Fr) may be applied individually for each polygonal element 80 or in combination as a combined reactive force ($Fr_{Total}$).

Similarities with the techniques described in FIGS. 13-15 for projected area 90 wherein the polygonal elements 80 are located in different planes also apply fully to the projected arc 200 method. For example, using projected arc 200 to compute the reactive forces ($Fr_A$), ($Fr_B$) at the outside corner would similarly provide a natural response to opposing the virtual boundary 55. Increases in the projected arc 200 translate into increases in reactive force (Fr) and decreases in projected arc 200 translate into decreases in reactive force (Fr). In so doing, the projected arc 200 technique avoids discrete jumps in reactive force (Fr) that move the tool 20 abruptly or unnaturally during encounters with the virtual boundary 55. Unexpected kick back of the tool 20 while rolling over the outside corner is mitigated. Thus, the projected arc 200 techniques described herein solve surface modeling issues relating to corners. The projected arc 200 techniques apply fully to any other examples wherein multiple non-planar polygonal elements 80 are simultaneously penetrated by the virtual volume 74. Examples include, but are not limited to, inside corners, peaks, valleys, etc.

C. Displaced Volume

Figure 18:
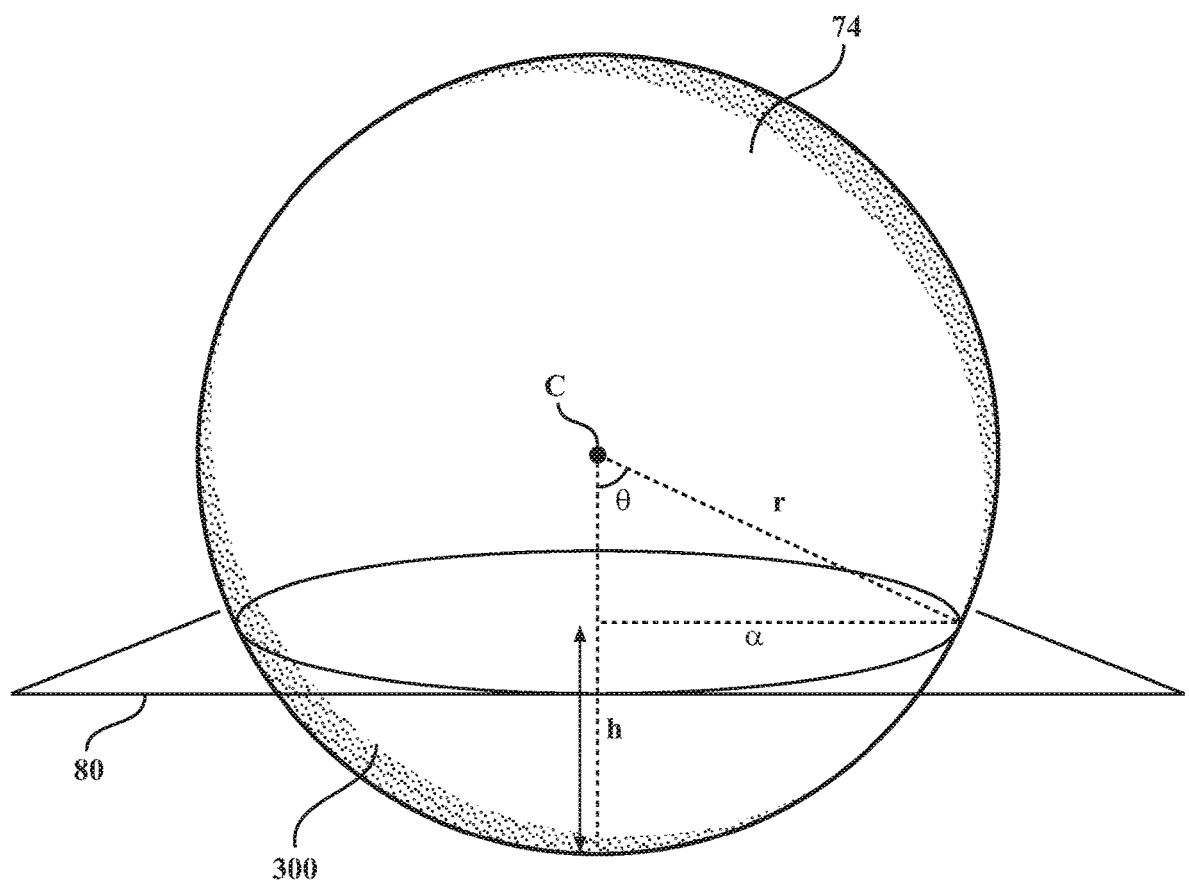
FIG. 18 illustrates one example of computing the penetration factor based on displaced volume with respect to one polygonal element of the virtual boundary.

In accordance with yet another example, as shown in FIG. 18, the controller 30 is configured to compute the reactive force (Fr) based on the penetration factor being related to a displaced volume 300 defined by a portion of the volume of the virtual volume 74 that penetrates the polygonal element 80 and wherein the displaced volume 300 is bound by the geometry of the polygonal element. The displaced volume 300 is defined by a combination of any volumetric portions of the virtual volume 74 being bound by the geometry of the polygonal element 80 during intersection of the virtual volume 74 with the polygonal element 80.

The displaced volume 300 is bound by the polygonal element 80. Specifically, the displaced volume 300 is bound by a perimeter of the polygonal element 80. In other words, the displaced volume 300 for a single polygonal element 80 is considered in as much as the displaced volume 300 exists within the perimeter of the polygonal element 80. This is so, even if the displaced volume 300 exists above or below the plane of the polygonal element 80 in Cartesian space.

The virtual volume 74 is defined such that the displaced volume 300 changes non-linearly relative to a linear depth of penetration (i.e., the distance by which the virtual volume 74 protrudes into the polygonal element 80 and/or virtual boundary 55) by the virtual volume 74. Although the reactive force (Fr) may change with changes in the linear depth of penetration, the reactive force (Fr) is computed based on the displaced volume 300 and without computationally accounting for the linear depth of penetration.

In this example, the reactive force (Fr) is related to the displaced volume 300. In one example, the reactive force (Fr) is directly correlated with the displaced volume 300. Additionally or alternatively, the reactive force (Fr) is proportional to the displaced volume 300.

The reactive force (Fr) may be applied as a vector being normal to the plane of the polygonal element 80. The location of the vector with respect to the plane of the polygonal element 80 may vary depending on the location of displaced volume 300 with respect to the polygonal element 80. The magnitude of the reactive force (Fr) may vary depending on the volumetric size of the displaced volume 300. The reactive force (Fr) vector may be at an angle that is not normal with respect to the plane of the polygonal element 80 depending on the displaced volume 300 and/or the pose of the virtual volume 74 during penetration. Techniques for computing the reactive force (Fr) from the displaced volume 300 are described below.

For comparative purposes, the spherical virtual volume 74 and the triangular polygonal element 80 are shown for computation of the displaced volume 300. Of course, other examples are possible. In FIG. 18, the virtual volume 74 penetrates the plane of the polygonal element 80 and creates the displaced volume 300 below the plane. Here, the displaced volume 300 takes the shape of a spherical cap or dome cut off by a plane of the polygonal element 80. In this example, c is the spherical center, h is the height of the displaced volume 300, and r is the radius of the sphere. Here, the plane of the polygonal element 80 passes through a portion short of the spherical center c. Had, the penetration reached the spherical center c, the height h of the displaced volume 300 would equal the radius r of the sphere, and the displaced volume 300 would be a hemisphere.

To compute the displaced volume 300 in this example, parameters of the virtual volume 74 and the displaced volume 300 are utilized. Such parameters include the radius r of the virtual volume 74, the height h of the displaced volume 300, and a radius a of the base 302 of the displaced volume 300 (at the plane of intersection). For example, the displaced volume 300 for a sphere may be computed using the equation $V_{displaced}=(\pi h^2/3)(3r-h)$. Alternatively, the displaced volume 300 may be computed using calculus techniques such as using integration under a surface of rotation for the displaced volume 300, or the like. Of course, computation of the displaced volume 300 will be different given shapes other than a sphere.

Again, since the displaced volume 300 is bound by the polygonal element 80, those portions of the virtual volume 74 that extend beyond the polygonal element 80 would not be taken into account to generate the reactive force (Fr) for the specific polygonal element 80 at hand. To bind the displaced volume 300 to the polygonal element, 80, in one example, adjacent polygonal elements 80 can be modeled as three-dimensional elements, such as adjacent triangular prisms (for triangles), corresponding to the perimeter of each polygonal element 80. Thus, if the penetrating virtual volume 74 extends across a triangular prism wall, only the portion of the virtual volume 74 within the triangular prism for the corresponding polygonal element 80 is taken into account to generate the reactive force (Fr) for that specific polygonal element 80. The portion of the virtual volume 74 that extended across the triangular prism wall is taken into account to generate the reactive force (Fr) for the adjacent polygonal element 80.

It should be reiterated that the calculations with respect to FIG. 18 are specific to a spherical virtual volume 74, and further specific to displaced volume 300 displaced completely within edges of the triangular polygonal element 80 and intersecting no vertices of the triangular polygonal element 80. Of course, the displaced volume 300 and hence the calculations for computing the displaced volume 300 may be different depending on the geometry of the polygonal element 80, the geometry of the virtual volume 74, and the relative locations of these geometries to each other. Furthermore, for the examples shown, computations of the displaced volume 300 will differ depending on how many edges (from 0 up to 3) and vertices (from 0 up to 3) of the triangular polygonal element 80 are implicated by the displaced volume 300. More complex displaced volumes 300 can be computed in instances where the virtual volume 74 is not spherical, but rather a spheroid, an ellipsoid, a toroid, or the like. Geometric computation of the displaced volume 300 is contemplated for any geometric configuration and situation other than those described herein.

As should be apparent based on FIG. 18, the displaced volume 300 also varies with respect to the linear depth of penetration, which in the example of FIG. 18, is the height h of the displaced volume 300. However, the displaced volume 300 does not change linearly with respect to linear depth of penetration because the penetrating body is volumetric and does not apply a linear impact force (Fa) to the polygonal element 80 and/or virtual boundary 55. Instead, the penetrating body applies a higher order impact force (Fa) as a function of the volumetric shape of the virtual volume 74. Accordingly, the displaced volume 300 changes with respect to linear depth of penetration according to this higher order volumetric function. Once again, the variable nature of the displaced volume 300 occurs in part because the virtual volume 74 in the examples shown in FIG. 18 has only one face (e.g., is spherical) and does not have identical cross-sectional areas adjacent to one another.

Thus, reactive forces (Fr) computed in response to penetration by the virtual volume 74 are variably responsive to the linear depth of penetration. However, even though the reactive force (Fr) may change with changes in the linear depth of penetration, the reactive force (Fr) is indeed computed based on the displaced volume 300 in this example. The reactive force (Fr) is not computed based simply on the linear depth, h, by which the virtual volume 74 protrudes into the polygonal element 80 and/or virtual boundary 55.

The examples and different possibilities described with respect to FIGS. 5-7 shown for projected area 90 may be fully understood with respect to displaced volume 300 and therefore are not repeated for simplicity. Of course, one skilled in the art would appreciate that reactive forces (Fr) computed based on displaced volume 300 are likely to be different as compared with those reactive forces (Fr) shown computed based on projected area 90. Furthermore, iterative application of reactive force (Fr) computed based on recalculation of displaced volume 300 is fully contemplated.

Furthermore, the examples of FIGS. 10-12 showing multiple reactive forces (e.g., $Fr_A$-$Fr_F$) computed using projected area 90 and generated in response to simultaneous penetration of multiple polygonal elements (e.g., 80A-80F) by the virtual volume 74 may be fully understood with respect to the techniques described herein using displaced volume 300. Mainly, each reactive force ($Fr_A$-$Fr_F$) would be related to the respective displaced volume 300 bound by each polygonal element 80A-80F. For displaced volume 300, the reactive forces (Fr) may be applied individually for each polygonal element 80 or in combination as a combined reactive force ($Fr_{Total}$).

Similarities with the techniques described in FIGS. 13-15 for projected area 90 wherein the polygonal elements 80 are located in different planes also apply fully to the displaced volume 300 method. For example, using displaced volume 300 to compute the reactive forces ($Fr_A$), ($Fr_B$) at the outside corner would similarly provide a natural response to opposing the virtual boundary 55. Increases in the displaced volume 300 translate into increases in reactive force (Fr) and decreases in displaced volume 300 translate into decreases in reactive force (Fr). In so doing, the displaced volume 300 technique avoids discrete jumps in reactive force (Fr) that move the tool 20 abruptly or unnaturally during encounters with the virtual boundary 55. Unexpected kick back of the tool 20 while rolling over the outside corner is mitigated. Thus, the displaced volume 300 techniques described herein solve surface modeling issues relating to corners. The displaced volume 300 techniques apply fully to any other examples wherein multiple non-planar polygonal elements 80 are simultaneously penetrated by the virtual volume 74. Examples include, but are not limited to, inside corners, peaks, valleys, etc.

D. Other Applications

Those skilled in the art appreciate that the above described examples of projected area, projected arc, and displaced volume each compute the reactive force (Fr) based on the penetration factor being a function of a geometry of the virtual volume 74 bound relative to a geometry (2D or 3D) of the polygonal element 80. However, it is fully contemplated that there are techniques other than those described herein for computing the reactive force (Fr) based on the penetration factor being a function of a geometry of the virtual volume 74 bound relative to a geometry of the polygonal element 80. For example, instead of projected arc, a projected perimeter may be utilized if the cross-sectional area 100 has no arc segments 202, or the like.

Any of the different surface modeling techniques described herein may be selectively turned off and on by the controller 30. For example, projected area 90 techniques may be reserved for traversing outside corners, while projected arc 200 techniques may be reserved for traversing a flat surface, etc. Such selection of these surface-modeling techniques may be based on, e.g., user input. The user may select the surface-modeling mode on the displays 38 or the user input device 40. In another example, the controller 30 automatically identifies what is occurring between the virtual volume 74 and the virtual boundary 55 and selects the surface-modeling mode based on predetermined settings stored in memory. For example, the controller 30 may automatically determine the situation based on how many, where, and what polygonal elements 80 have been penetrated by the virtual volume 74.

Furthermore, it is contemplated to blend any of the different surface modeling techniques described herein. This is possible because the techniques all utilize the penetration factor being a function of a geometry of the virtual volume 74 bound relative to a geometry of the polygonal element 80. Thus, any combination of projected area 90, projected arc 200 and/or displaced volume 300 modes may be utilized simultaneously to derive the reactive force (Fr) for any given polygonal element 80.

The techniques described herein may be utilized for several practical applications or situations for the robotic surgical system 10. For example, the robotic surgical system 10 may be utilized in a manual mode of operation. During the manual mode, the operator manually directs, and the manipulator 14 controls, movement of the tool 20. The operator physically contacts the tool 20 to cause movement of the tool 20. The controller 30 monitors the forces and/or torques placed on the tool 20 using the force-torque sensor 70. The virtual boundary 55 may delineate areas of the anatomy to be treated from areas that should be avoided. Alternatively or additionally, the virtual boundary 55 may be provide a guide for directing the operator to move the tool 20 manually towards the target site. In yet another example, the virtual boundary 55 is defined relative to an object (e.g., equipment) to be avoided. In any of these instances, if manual operation responsive to the forces and/or torques detected by the force-torque sensor 70 result in penetration of the virtual boundary 55, the controller 30 may control the manipulator 14 to move the tool 20 away from the virtual boundary 55. In turn, this provides the operator with a haptic sense of the location of the virtual boundary 55 in effort to avoid the same in the manual mode.

In another application, the controller 30 may command the manipulator 14 to direct autonomous movement of the tool 20 in an autonomous mode of operation. Here, the manipulator 14 is capable of moving the tool 20 free of operator assistance. Free of operator assistance may mean that an operator does not physically contact the tool 20 to apply force to move the tool 20. Instead, the operator may use some form of control to manage starting and stopping of movement. For example, the operator may hold down a button of a remote control to start movement of the tool 20 and release the button to stop movement of the tool 20. In one instance, the positioning of the tool 20 is maintained on the tool path during autonomous mode but the operator may desire to re-orient the tool 20. Reorientation of the tool 20, while maintaining position, may implicate one or more virtual boundaries 55. By accounting for the updated orientation of the tool 20 and the virtual boundary 55 in the virtual simulation 72, the system 10 and method can react, e.g., to undesired collisions between the re-oriented tool 20 and objects in the vicinity and/or objects interfering with the path of movement of the re-oriented tool 20. In another example, the virtual boundary 55 is provided in the autonomous mode as an added precaution in the event that autonomous movement may be inadvertently altered. Those skilled in the art will appreciate that various other applications or situations may utilize the projected area techniques described herein.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A robotic system comprising:
   a tool;
   a manipulator comprising a plurality of links and configured to move the tool; and
   a controller coupled to the manipulator and configured to implement a virtual simulation wherein the tool is represented as a virtual volume being adapted to interact relative to a virtual boundary defined by a mesh of polygonal elements, each of the polygonal elements comprising a plane and a perimeter, and wherein the controller is configured to:
   compute a reactive force in response to penetration of one of the polygonal elements by the virtual volume in the virtual simulation, wherein the reactive force is computed based on a penetration factor being a function of a planar intersection between the virtual volume and the plane of the polygonal element, wherein the planar intersection is bound by the perimeter of the polygonal element;
   apply the reactive force to the virtual volume in the virtual simulation to reduce penetration of the polygonal element by the virtual volume; and
   command the manipulator to move the tool in accordance with application of the reactive force to the virtual volume in the virtual simulation to constrain movement of the tool relative to the virtual boundary.

2. The robotic system of claim 1, wherein the penetration factor is functionally independent of a linear depth of penetration of the polygonal element by the virtual volume.

3. The robotic system of claim 1, further comprising a navigation system configured to track states of the tool and being coupled to the controller and wherein the virtual volume is positioned based on tracked states of the tool, wherein the tool is configured to interact with a target site and wherein the navigation system is configured to track states of the target site and wherein the virtual boundary is associated with the target site.

4. The robotic system of claim 1, further comprising a navigation system configured to track states of the tool and being coupled to the controller and wherein the virtual volume is positioned based on tracked states of the tool, wherein the navigation system is configured to track states of an object to be avoided by the tool and wherein the virtual boundary is associated with the object to be avoided.

5. The robotic system of claim 1, wherein the controller is further configured to compute multiple reactive forces in response to simultaneous penetration of multiple polygonal elements by the virtual volume in the virtual simulation, wherein each reactive force is computed based on the penetration factor being a function of the planar intersection between the virtual volume and the plane of each polygonal element, wherein each planar intersection is bound by the perimeter of each polygonal element.

6. The robotic system of claim 5, wherein the controller is further configured to:
simultaneously apply the multiple reactive forces to the virtual volume in the virtual simulation; and
command positioning of the manipulator in accordance with application of the multiple reactive forces to the virtual volume in the virtual simulation.

7. The robotic system of claim 5, wherein the controller is further configured to:
combine the multiple reactive forces to generate a combined reactive force;
apply the combined reactive force to the virtual volume in the virtual simulation; and
command positioning of the manipulator in accordance with application of the combined reactive force to the virtual volume in the virtual simulation.

8. The robotic system of claim 7, wherein the controller is further configured to apply a weighting factor to each of the reactive forces such that the combined reactive force is constant for any given simultaneous penetration of multiple polygonal elements by the virtual volume.

9. The robotic system of claim 1, further comprising a force-torque sensor being configured to sense an input force applied to the tool and wherein the input force is applied to the virtual volume in the virtual simulation to cause penetration of one of the polygonal elements by the virtual volume.

10. The robotic system of claim 1, wherein the penetration factor is further defined as a function of an area defined by the planar intersection between the virtual volume and the plane of the polygonal element, wherein the area is bound by the perimeter of the polygonal element.

11. The robotic system of claim 1, wherein the penetration factor is further defined as a function of one or more arcs of a shape defined by the planar intersection between the virtual volume and the plane of the polygonal element, wherein the one or more arcs are bound by the perimeter of the polygonal element.

12. A method of controlling a robotic system comprising a tool, a manipulator comprising a plurality of links and configured to move the tool, and a controller coupled to the manipulator and configured to implement a virtual simulation wherein the tool is represented as a virtual volume being configured to interact relative to a virtual boundary defined by a mesh of polygonal elements, each of the polygonal elements comprising a plane and a perimeter, the method comprising the controller:
computing a reactive force in response to penetration of one of the polygonal elements by the virtual volume in the virtual simulation, wherein the reactive force is computed based on a penetration factor being a function of a planar intersection between the virtual volume and the plane of the polygonal element, wherein the planar intersection is bound by the perimeter of the polygonal element;
applying the reactive force to the virtual volume in the virtual simulation for reducing penetration of the polygonal element by the virtual volume; and
commanding the manipulator for moving the tool in accordance with application of the reactive force to the virtual volume in the virtual simulation for constraining movement of the tool relative to the virtual boundary.

13. The method of claim 12, wherein the penetration factor is functionally independent of a linear depth of penetration of the polygonal element by the virtual volume.

14. The method of claim 12 further comprising:
receiving, from a navigation system, tracked states of the tool;
positioning the virtual volume based on tracked states of the tool;
commanding the manipulator for moving the tool in relation to a target site;
receiving, from the navigation system, tracked states of the target site; and
associating the virtual boundary with the target site.

15. The method of claim 12 further comprising:
receiving, from a navigation system, tracked states of the tool;
positioning the virtual volume based on tracked states of the tool;
receiving, from the navigation system, tracked states of an object to be avoided by the tool; and
associating the virtual boundary with the object to be avoided.

16. The method of claim 12, further comprising computing multiple reactive forces in response to simultaneous penetration of multiple polygonal elements by the virtual volume in the virtual simulation, wherein each reactive force is computed based on the penetration factor being a function of the planar intersection between the virtual volume and the plane of each polygonal element, wherein each planar intersection is bound by the perimeter of each polygonal element.

17. The method of claim 16, further comprising:
simultaneously applying the multiple reactive forces to the virtual volume in the virtual simulation; and
commanding positioning of the manipulator in accordance with application of the multiple reactive forces to the virtual volume in the virtual simulation.

18. The method of claim 16, further comprising:
combining the multiple reactive forces for generating a combined reactive force;
applying the combined reactive force to the virtual volume in the virtual simulation; and
commanding positioning of the manipulator in accordance with application of the combined reactive force to the virtual volume in the virtual simulation.

19. The method of claim 18, further comprising applying a weighting factor to each of the reactive forces such that the combined reactive force is constant for any given simultaneous penetration of multiple polygonal elements by the virtual volume.

20. The method of claim 12, further comprising:
determining an input force applied to the tool based on measurements from a force-torque sensor, and
applying the input force to the virtual volume in the virtual simulation for causing penetration of one of the polygonal elements by the virtual volume.

21. The method of claim 12, wherein computing the reactive force is based on the penetration factor further defined as being a function of an area defined by the planar intersection between the virtual volume and the plane of the polygonal element, wherein the area is bound by the perimeter of the polygonal element.

22. The method of claim 12, wherein computing the reactive force is based on the penetration factor further defined as being a function of one or more arcs of a shape defined by the planar intersection between the virtual volume and the plane of the polygonal element, wherein the one or more arcs are bound by the perimeter of the polygonal element.

23. A controller-implemented method of simulating dynamics of a tool of a robotic system, the method comprising:
- simulating the tool as a virtual volume;
- simulating a virtual boundary comprising a mesh of polygonal elements;
- simulating movement of the virtual volume to penetrate multiple polygonal elements simultaneously;
- computing multiple reactive forces in response to simultaneous penetration of the multiple polygonal elements, wherein each reactive force is computed based on a penetration factor being a function of a geometry of the virtual volume bound relative to a geometry of each polygonal element;
- combining the multiple reactive forces for generating a combined reactive force;
- applying a weighting factor to each of the reactive forces such that the combined reactive force is constant for any given simultaneous penetration of multiple polygonal elements by the virtual volume; and
- simulating application of the combined reactive force to the virtual volume.

* * * * *